(12) United States Patent
Dyballa et al.

(10) Patent No.: US 9,221,850 B2
(45) Date of Patent: Dec. 29, 2015

(54) MONOPHOSPHITE LIGANDS HAVING A TERT-BUTYLOXYCARBONYL GROUP

(71) Applicants: Katrin Marie Dyballa, Recklinghausen (DE); Robert Franke, Marl (DE); Dieter Hess, Marl (DE); Dirk Fridag, Haltern am See (DE); Frank Geilen, Haltern am See (DE)

(72) Inventors: Katrin Marie Dyballa, Recklinghausen (DE); Robert Franke, Marl (DE); Dieter Hess, Marl (DE); Dirk Fridag, Haltern am See (DE); Frank Geilen, Haltern am See (DE)

(73) Assignee: EVONIK INDUSTRIES AG, Essen (DE)

( * ) Notice: Subject to any disclaimer, the term of this patent is extended or adjusted under 35 U.S.C. 154(b) by 0 days.

(21) Appl. No.: 14/715,334

(22) Filed: May 18, 2015

(65) Prior Publication Data

US 2015/0336988 A1 Nov. 26, 2015

(30) Foreign Application Priority Data

May 20, 2014 (DE) .......................... 10 2014 209 532

(51) Int. Cl.
| | |
|---|---|
| *C07F 9/141* | (2006.01) |
| *C07F 15/00* | (2006.01) |
| *C07C 45/50* | (2006.01) |
| *B01J 31/22* | (2006.01) |

(52) U.S. Cl.
CPC ............. *C07F 9/141* (2013.01); *B01J 31/2221* (2013.01); *C07C 45/505* (2013.01); *C07F 15/0073* (2013.01)

(58) Field of Classification Search
USPC ............................. 556/13; 558/197; 568/454
See application file for complete search history.

(56) References Cited

U.S. PATENT DOCUMENTS

2011/0230620 A1  9/2011  Tunge et al.
2014/0309423 A1  10/2014 Christiansen et al.

FOREIGN PATENT DOCUMENTS

| DE | 10 2011 085 883 A1 | 5/2013 |
| EP | 0 614 870 A2 | 9/1994 |
| EP | 0 614 870 A3 | 9/1994 |
| WO | WO 2010/057099 A1 | 5/2010 |

OTHER PUBLICATIONS

Extended European Search Report issued Aug. 6, 2015 in Patent Application No. 15166027.1.
Rui M.B. Carrilho, et al., "Rhodium/tris-binaphthyl chiral monophosphite complexes: Efficient catalysts for the hydroformylation of disubstituted aryl olefins" Journal of Organometallic Chemistry, vol. 698, 2012, pp. 28-34.
Konstantin N. Gavrilov, et al., "Phosphites and diamidophosphites based on mono-ethers of BINOL: a comparison of enantioselectivity in asymmetric catalytic reactions" Tetrahedron, vol. 68, 2012, pp. 1581-1589.
Ana Z. González, et al., "Gold(I)-Catalyzed Enantioselective [4+2]-Cycloaddition of Allene-dienes" Organic Letters, vol. 12, No. 1, 2010, pp. 200-203.
Detlef Selent, et al., "Novel Oxyfunctionalized Phosphonite Ligands for the Hydroformylation of Isomeric *n*-Olefins" Communications, Angew. Chem. Int. Ed. 2000, vol. 39 No. 9, pp. 1639-1641.
Robert Franke, et al., "Applied Hydroformylation" American Chemical Society, 2012, pp. 5675-5732.
Hugo Tricas, et al., "Bulky monophosphite ligands for ethene hydroformylation" Journal of Catalysis, vol. 298, 2013, pp. 198-205.

*Primary Examiner* — Porfirio Nazario Gonzalez
(74) *Attorney, Agent, or Firm* — Oblon, McClelland, Maier & Neustadt, L.L.P.

(57) ABSTRACT

A novel monophosphite ligand having a tert-butyloxycarbonyl group is useful as a ligand in hydroformylation of an olefin.

18 Claims, No Drawings

MONOPHOSPHITE LIGANDS HAVING A TERT-BUTYLOXYCARBONYL GROUP

FIELD OF THE INVENTION

The invention relates to a novel monophosphite ligand having a tert-butyloxycarbonyl group), to use thereof as ligand in hydroformylation and to the hydroformylation process.

DISCUSSION OF THE BACKGROUND

The reactions between olefin compounds, carbon monoxide and hydrogen in the presence of a catalyst to give the aldehydes comprising one additional carbon atom are known as hydroformylation or oxo synthesis. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

The disadvantage of bi- and polydentate phosphine ligands is a relatively high level of complexity necessary for preparation thereof. It is therefore often unfeasible to use such systems in industrial operations. An additional factor is comparatively low activity, which has to be compensated for by chemical engineering, through high residence times. This in turn leads to unwanted side reactions of the products.

In Angew. Chem. Int. Ed. 2000, 39, No. 9, p. 1639-1641, Börner et al. describe ligands having one P—C bond and two P—O bonds; these are thus phosphonites. The phosphonites described therein, when used in hydroformylation, have n/iso selectivities (n/iso=the ratio of linear aldehyde (=n) to branched (=iso) aldehyde)) of 0.61 to 1.57.

The phosphonite ligands described in DE 199 54 721 have a good n/iso selectivity. However, in-house studies have shown that the compound II-c (in DE 199 54 721; page 6) has a tendency to photochemically induced breakdown, and should therefore not be used on the industrial scale.

One disadvantage of the ligands having a phosphonite structure is that their preparation is very complex. However, the possibility of a favourable and simple synthesis is crucial for the use of ligands in an industrial scale process.

Ease of availability and the associated good possibility of industrial scale use is an important criterion, since the preparation complexity and the associated production costs for the ligand may only be so high that the viability of the overall process in which the ligand is to be used at a later stage is still assured.

Rhodium-monophosphite complexes in catalytically active compositions are suitable for the hydroformylation of branched olefins having internal double bonds.

Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally hydroformylated compounds is in need of improvement.

EP 0 155 508 discloses the use of bisarylene-substituted monophosphites in the rhodium-catalysed hydroformylation of sterically hindered olefins, e.g. isobutene. However, rhodium concentrations used here are sometimes very high (one being 250 ppm), which is unacceptable for an industrial scale process in view of the current cost of rhodium and has to be improved.

For hydroformylation reactions, tris(2,4-di-tert-butylphenyl)phosphite (TDTBPP) is currently one of the best-performing monophosphite ligands commercially available, and is available under the Alkanox 240 trade name (see also R. Franke, D. Selent, A. Börner, "Applied Hydroformylation", Chem. Rev., 2012, 112, p. 5681, chapter 3.4.2).

SUMMARY OF THE INVENTION

The technical object that formed the basis of the present invention is that of providing a novel monophosphite ligand which does not have the above-detailed disadvantages from the related art in the hydroformylation of unsaturated compounds.

Firstly, the preparation complexity should be lower than for the above-described phosphonite ligands; secondly, a good n selectivity should be achieved in relation to the hydroformylation.

More particularly, the novel monophosphite ligands should also be suitable for hydroformylation of industrial olefin mixtures containing mainly branched olefins having internal double bonds. In the hydroformylation, at the same time, a high proportion of desired terminally hydroformylated products should be obtained.

The above and other objects are achieved by a ligand having structure I or II:

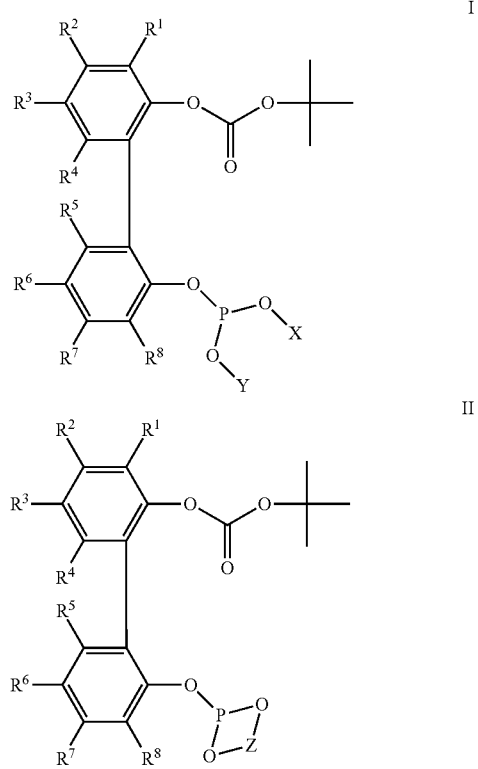

wherein $R^1$, $R^2$, $R^3$, $R^4$, $R^5$, $R^6$, $R^7$, $R^8$ are each independently selected from the group consisting of: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, and —N[($C_1$-$C_{12}$)-alkyl]$_2$;

X and Y are each independently selected from the group consisting of

—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, and —($C_5$-$C_8$)-cycloalkyl-($C_4$-$C_{20}$)-aryl-CO—($C_6$-$C_{20}$)-aryl, Z is selected from the group consisting of —($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_{20}$)-aryl-, —($C_4$-$C_{20}$)-heteroaryl-, —($C_6$-$C_{20}$)-aryl-CO—($C_6$-$C_{20}$)-aryl-, and —($C_6$-$C_{20}$)-aryl-($C_6$-$C_{20}$)-aryl-;

wherein the alkyl, heteroalkyl, cycloalkyl, heterocycloalkyl, aryl and heteroaryl groups mentioned are optionally substituted.

In another embodiment, the present invention relates to a complex, comprising:

the above ligand, and a metal atom selected from the group consisting of Rh, Ru, Co, and Ir.

In another embodiment, the present invention relates to a process for the hydroformylation of an olefin, comprising:

a) initially charging an olefin, b) adding the above complex, to obtain a reaction mixture, c) feeding $H_2$ and CO into the reaction mixture, d) heating the reaction mixture, to obtain conversion of the olefin to an aldehyde.

In another embodiment, the present invention relates to a process for the hydroformylation of an olefin, comprising:

a) initially charging an olefin, b) adding the above ligand and a compound including a metal atom selected from the group consisting of Rh, Ru, Co, and Ir, to obtain a reaction mixture, c) feeding $H_2$ and CO into the reaction mixture, d) heating the reaction mixture, to obtain conversion of the olefin to an aldehyde.

DETAILED DESCRIPTION OF THE INVENTION

The present invention relates to a ligand having one of the two general structures I and II:

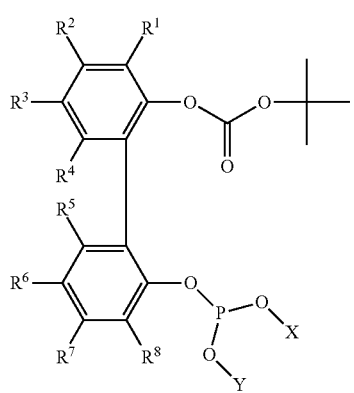

I

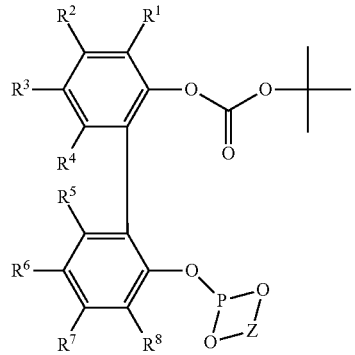

II wherein $R^1$, $R^2$, $R^3$, $R^4$, $R^5$, $R^6$, $R^7$, $R^8$ are each independently selected from: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen (such as Cl, F, Br, I), COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

X and Y are each independently selected from:

—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, —($C_5$-$C_8$)-cycloalkyl, —($C_6$-$C_{20}$)-aryl-CO—($C_6$-$C_{20}$)-aryl, Z is selected from:

—($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_{20}$)-aryl-, —($C_4$-$C_{20}$)-heteroaryl-, —($C_6$-$C_{20}$)-aryl-CO—($C_6$-$C_{20}$)-aryl-, —($C_6$-$C_{20}$)-aryl-($C_6$-$C_{20}$)-aryl-;

where the alkyl, heteroalkyl, cycloalkyl, heterocycloalkyl, aryl and heteroaryl groups mentioned may be substituted.

($C_1$-$C_{12}$)-Alkyl and O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_3$-$C_{12}$)-Cycloalkyl and ($C_3$-$C_{12}$)-heterocycloalkyl may each be unsubstituted or substituted by one or more identical or different radicals selected from ($C_1$-$C_{12}$)-alkyl, ($C_1$-$C_{12}$)-alkoxy, ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_6$-$C_{20}$)-Aryl and —($C_6$-$C_{20}$)-aryl-($C_6$-$C_{20}$)-aryl- may each be unsubstituted or substituted by one or more identical or different radicals selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]2.

In the context of the invention, the expression —($C_1$-$C_{12}$)-alkyl encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression —$(C_1$-$C_{12})$-alkyl also apply to the alkyl groups in —O—$(C_1$-$C_{12})$-alkyl, i.e. in —$(C_1$-$C_{12})$-alkoxy. Preferably, these groups are unsubstituted straight-chain or branched —$(C_1$-$C_6)$-alkoxy groups.

Substituted —$(C_1$-$C_{12})$-alkyl groups and substituted —$(C_1$-$C_{12})$-alkoxy groups may have one or more substituents, depending on their chain length. The substituents are preferably each independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl.

The expression "—$(C_3$-$C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3$-$C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3$-$C_{12})$-heterocycloalkyl groups are tetrahydrothiophenyl, tetrahydrofuryl, tetrahydropyranyl and dioxanyl.

Substituted —$(C_3$-$C_{12})$-cycloalkyl groups and substituted —$(C_3$-$C_{12})$-heterocycloalkyl groups may have one or more (e.g. 1, 2, 3, 4 or 5) further substituents, depending on their ring size. These substituents are preferably each independently selected from —$(C_1$-$C_{12})$-alkyl, —$(C_1$-$C_{12})$-alkoxy, —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl. Substituted —$(C_3$-$C_{12})$-cycloalkyl groups preferably bear one or more —$(C_1$-$C_6)$-alkyl groups. Substituted —$(C_3$-$C_{12})$-heterocycloalkyl groups preferably bear one or more —$(C_1$-$C_6)$-alkyl groups.

In the context of the present invention, the expression —$(C_6$-$C_{20})$-aryl and —$(C_6$-$C_{20})$-aryl-$(C_6$-$C_{20})$-aryl- encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6$-$C_{10})$-aryl and —$(C_6$-$C_{10})$-aryl-$(C_6$-$C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6$-$C_{20})$-aryl groups and —$(C_6$-$C_{20})$-aryl-$(C_6$-$C_{20})$-aryl groups may have one or more (e.g. 1, 2, 3, 4 or 5) substituents, depending on their ring size. These substituents are preferably each independently selected from —H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen (such as Cl, F, Br, I), —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, —N[$(C_1$-$C_{12})$-alkyl]$_2$.

Substituted —$(C_6$-$C_{20})$-aryl groups and —$(C_6$-$C_{20})$-aryl-$(C_6$-$C_{20})$-aryl groups are preferably substituted —$(C_6$-$C_{10})$-aryl groups and —$(C_6$-$C_{10})$-aryl-$(C_6$-$C_{10})$-aryl groups, especially substituted phenyl or substituted naphthyl or substituted anthracenyl. Substituted —$(C_6$-$C_{20})$-aryl groups preferably bear one or more, for example 1, 2, 3 or 5, substituents selected from —$(C_1$-$C_{12})$-alkyl groups, —$(C_1$-$C_{12})$-alkoxy groups.

Any ranges mentioned herein include all values and subvalues of between the lower and upper limits of the range.

In one embodiment, X and Y are each independently selected from:
—$(C_1$-$C_{12})$-alkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_6$-$C_{20})$-aryl-COO—$(C_1$-$C_{12})$-alkyl, —$(C_6$-$C_{20})$-aryl-CONH—$(C_1$-$C_{12})$-alkyl, —$(C_6$-$C_{20})$-aryl-CON[$(C_1$-$C_{12})$-alkyl]$_2$, —$(C_4$-$C_{20})$-heteroaryl, —$(C_4$-$C_{20})$-heteroaryl-$(C_1$-$C_{12})$-alkyl.

In one embodiment, X and Y are each independently selected from:
—$(C_1$-$C_{12})$-alkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_6$-$C_{20})$-aryl-COO—$(C_1$-$C_{12})$-alkyl.

In one embodiment, X and Y are each independently selected from:
—$(C_1$-$C_{12})$-alkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl.

In one embodiment, Z is selected from:
—$(C_1$-$C_{12})$-alkyl-, —$(C_6$-$C_{20})$-aryl-, —$(C_6$-$C_{20})$-aryl-$(C_1$-$C_{12})$-alkyl-, —$(C_6$-$C_{20})$-aryl-CO—$(C_6$-$C_{20})$-aryl-, —$(C_1$-$C_{12})$-alkyl-$(C_6$-$C_{20})$-aryl-, —$(C_6$-$C_{20})$-aryl-$(C_6$-$C_{20})$-aryl-.

In one embodiment, Z is:

In one embodiment, Z is:
—$(C_6$-$C_{20})$-aryl-$(C_6$-$C_{20})$-aryl-.

In one embodiment, $R^1$, $R^2$, $R^3$, $R^4$, $R^5$, $R^6$, $R^7$, $R^8$ are each independently selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —NH$_2$, —N[$(C_1$-$C_{12})$-alkyl]$_2$.

In one embodiment, $R^1$, $R^2$, $R^3$, $R^4$, $R^5$, $R^6$, $R^7$, $R^8$ are each independently selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —COO—$(C_1$-$C_{12})$-alkyl, —N[$(C_1$-$C_{12})$-alkyl]$_2$.

In one embodiment, $R^1$, $R^2$, $R^3$, $R^4$, $R^5$, $R^6$, $R^7$, $R^8$ are each independently selected from:
—H, —$(C_1$-$C_{12})$-alkyl, —O—$(C_1$-$C_{12})$-alkyl, —$(C_6$-$C_{20})$-aryl.

In one embodiment, X and Y are the same radicals.

In one embodiment, $R^3$ and $R^6$ are each —O—$(C_1$-$C_{12})$-alkyl.

In one embodiment, $R^3$ and $R^6$ are each —OMe.

In one embodiment, $R^1$ and $R^8$ are each —$(C_1$-$C_{12})$-alkyl.

In one embodiment, $R^1$ and $R^8$ are each tert-butyl.

In one embodiment, $R^1$, $R^3$, $R^6$ and $R^8$ are each —($C_1$-$C_{12}$)-alkyl.

In one embodiment, $R^1$, $R^3$, $R^6$ and $R^8$ are each methyl.

In one embodiment, $R^1$, $R^3$, $R^6$ and $R^8$ are each tert-butyl.

In one embodiment, $R^1$, $R^2$, $R^3$, $R^4$, $R^5$, $R^6$, $R^7$ and $R^8$ are each —H.

In one embodiment, the ligand has the general structure III:

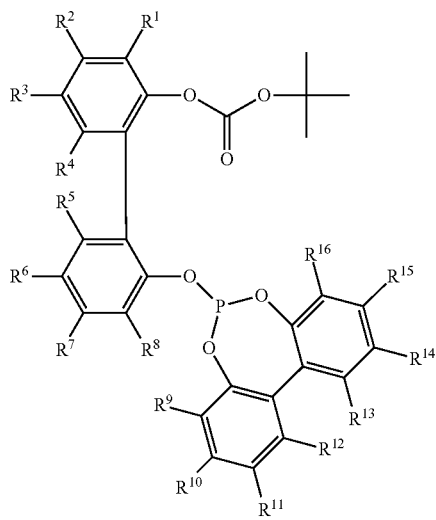

III where $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —NH$_2$, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —($C_6$-$C_{20}$)-aryl, where alkyl comprises 1-12 carbon atoms, preferably 1-10 carbon atoms, for example primary, secondary or tertiary alkyl groups such as methyl, ethyl, n-propyl, isopropyl, butyl, sec-butyl, t-butyl, t-butylethyl, t-butylpropyl, n-hexyl, amyl, sec-amyl, t-amyl, isooctyl, 2-ethylhexyl, decyl, dodecyl and octadecyl groups.

In one embodiment, $R^{11}$ and $R^{14}$ are each —O—($C_1$-$C_{12}$)-alkyl.

In one embodiment, $R^{11}$ and $R^{14}$ are each —OMe.

In one embodiment, $R^9$ and $R^{16}$ are each —($C_1$-$C_{12}$)-alkyl.

In one embodiment, $R^9$ and $R^{16}$ are each tert-butyl.

In one embodiment, $R^9$, $R^{11}$, $R^{14}$ and $R^{16}$ are each —($C_1$-$C_{12}$)-alkyl.

In one embodiment, $R^9$, $R^{11}$, $R^{14}$ and $R^{16}$ are each methyl.

In one embodiment, $R^9$, $R^{11}$, $R^{14}$ and $R^{16}$ are each tert-butyl.

In one embodiment, $R^9$, $R^{10}$, $R^{11}$, $R^{12}$, $R^{13}$, $R^{14}$, $R^{15}$ and $R^{16}$ are each —H.

In one embodiment, the ligand has the general structure IV:

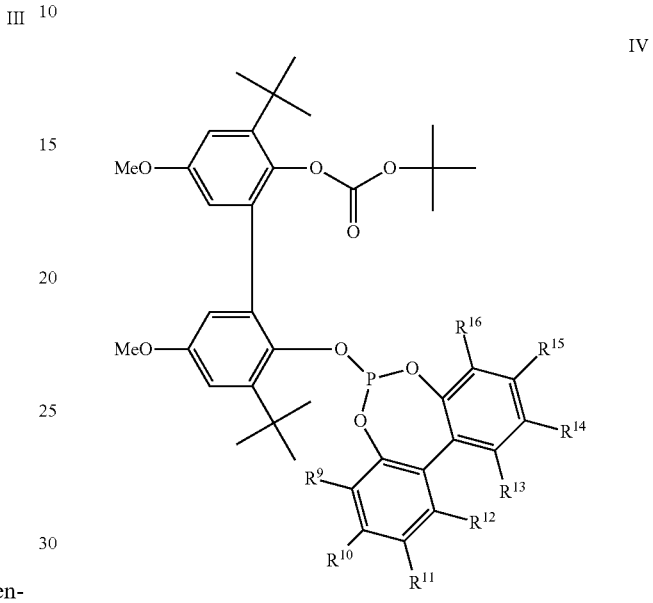

IV where $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —NH$_2$, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —N[($C_1$-$C_{12}$)-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —($C_6$-$C_{20}$)-aryl;

where alkyl comprises 1-18 carbon atoms, preferably 1-10 carbon atoms, for example primary, secondary or tertiary alkyl groups such as methyl, ethyl, n-propyl, isopropyl, butyl, sec-butyl, t-butyl, t-butylethyl, t-butylpropyl, n-hexyl, amyl, sec-amyl, t-amyl, isooctyl, 2-ethylhexyl, decyl, dodecyl and octadecyl groups.

In one embodiment, $R^{11}$ and $R^{14}$ are each —O—($C_1$-$C_{12}$)-alkyl.

In one embodiment, $R^{11}$ and $R^{14}$ are each —OMe.

In one embodiment, $R^9$ and $R^{16}$ are each —($C_1$-$C_{12}$)-alkyl.

In one embodiment, $R^9$ and $R^{16}$ are each tert-butyl.

In one embodiment, $R^9$, $R^{11}$, $R^{14}$ and $R^{16}$ are each —($C_1$-$C_{12}$)-alkyl.

In one embodiment, $R^9$, $R^{11}$, $R^{14}$ and $R^{16}$ are each methyl.

In one embodiment, $R^9$, $R^{11}$, $R^{14}$ and $R^{16}$ are each tert-butyl.

In one embodiment, $R^9$, $R^{10}$, $R^{11}$, $R^{12}$, $R^{13}$, $R^{14}$, $R^{15}$ and $R^{16}$ are each —H.

As well as the ligands, also claimed is a complex comprising these ligands.

Complex comprising:
an above-described ligand,
a metal atom selected from: Rh, Ru, Co, Ir.
In a preferred embodiment, the metal is Rh.

In this regard, see R. Franke, D. Selent, A. Bmrner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff, p. 233 ff. and references cited therein, and also K. D. Wiese and D. Obst in Top. Organomet. Chem. 2006, 18, 1-13; Springer Verlag Berlin Heidelberg 2006 p. 6 ff and references cited therein.

Additionally claimed is the use of the ligand as ligand in a ligand-metal complex for catalysis of a hydroformylation reaction.

Use of an above-described ligand in a ligand-metal complex for catalysis of a hydroformylation reaction.

The process in which the ligand is used as ligand in a ligand-metal complex for conversion of an olefin to an aldehyde is likewise claimed.

Process comprising the process steps of:
a) initially charging an olefin,
b) adding an above-described complex,
or an above-described ligand and a compound including a metal atom selected from: Rh, Ru, Co, Ir,
c) feeding in $H_2$ and CO,
d) heating the reaction mixture, with conversion of the olefin to an aldehyde.

In this process, process steps a) to d) can be effected in any desired sequence.

The reaction is conducted under customary conditions.

Preference is given to a temperature of 80° C. to 160° C. and a pressure of 1 to 300 bar.

Particular preference is given to a temperature of 100° C. to 160° C. and a pressure of 15 to 250 bar.

In a preferred embodiment, the metal is Rh.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The process according to the invention using the ligands according to the invention can be used to hydroformylate α-olefins, terminally branched, internal and internally branched olefins. What is remarkable is the high yield of terminally hydroformylated olefin, even when only a small proportion of olefins having a terminal double bond was present in the reactant.

The invention is to be illustrated in detail hereinafter by working examples.

Having generally described this invention, a further understanding can be obtained by reference to certain specific examples which are provided herein for purposes of illustration only, and are not intended to be limiting unless otherwise specified.

EXAMPLES

The following seventy structures (1 to 70) show possible working examples of the ligand:

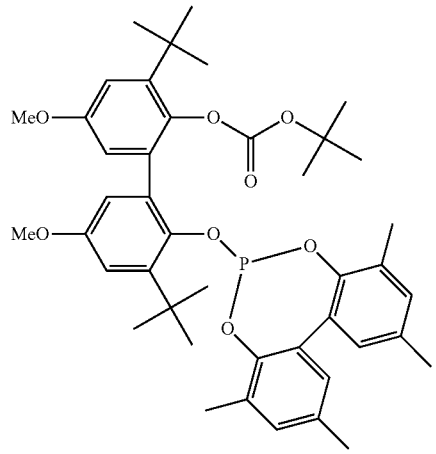

1

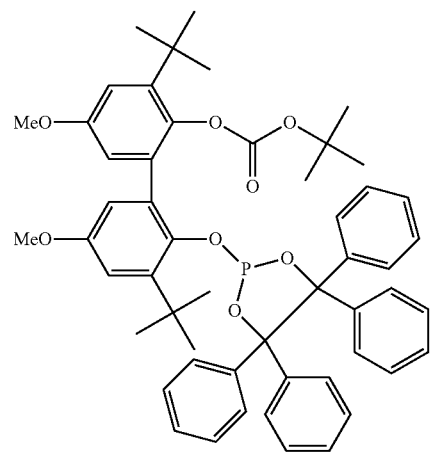

2

3
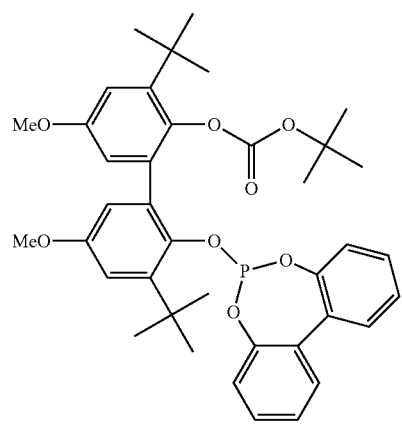
4
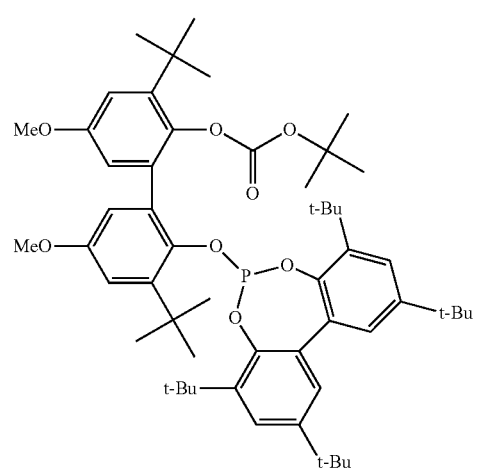
5
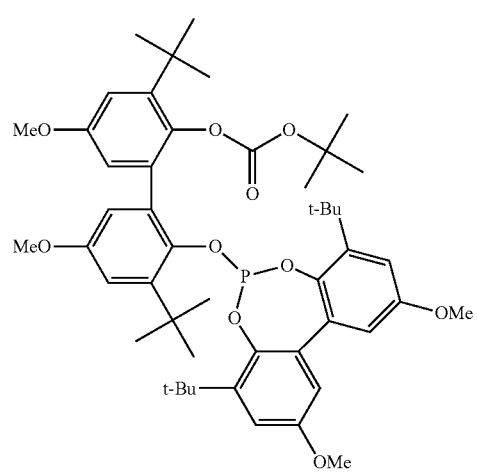
6
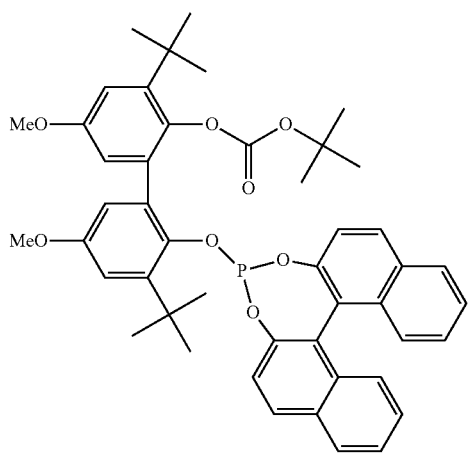
7
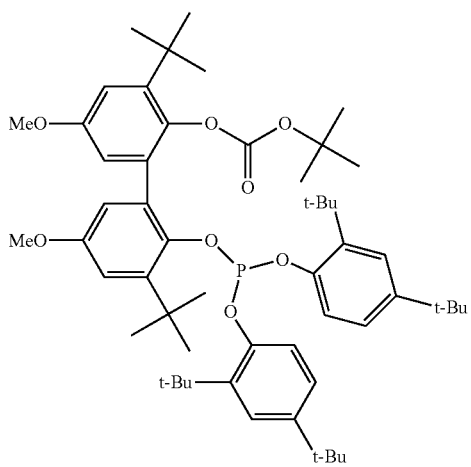
8
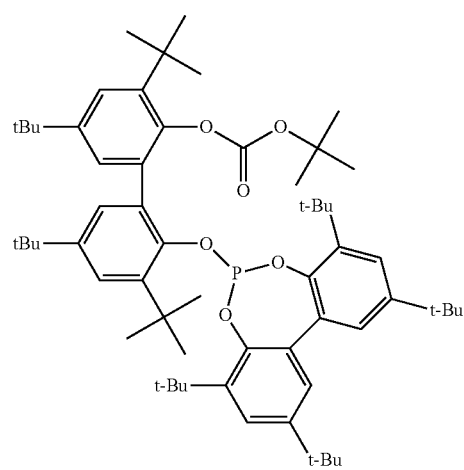

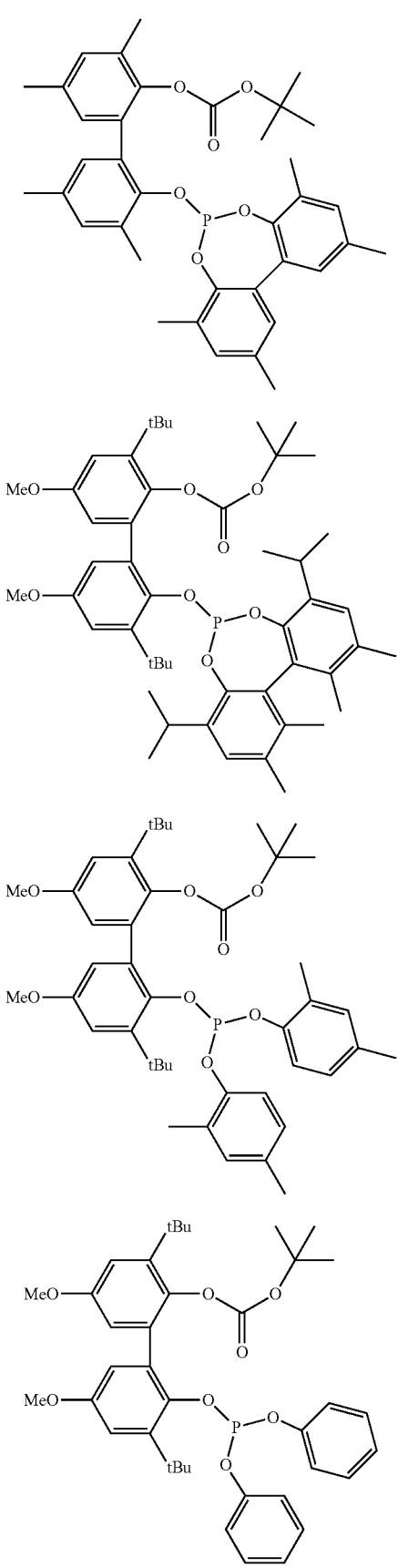
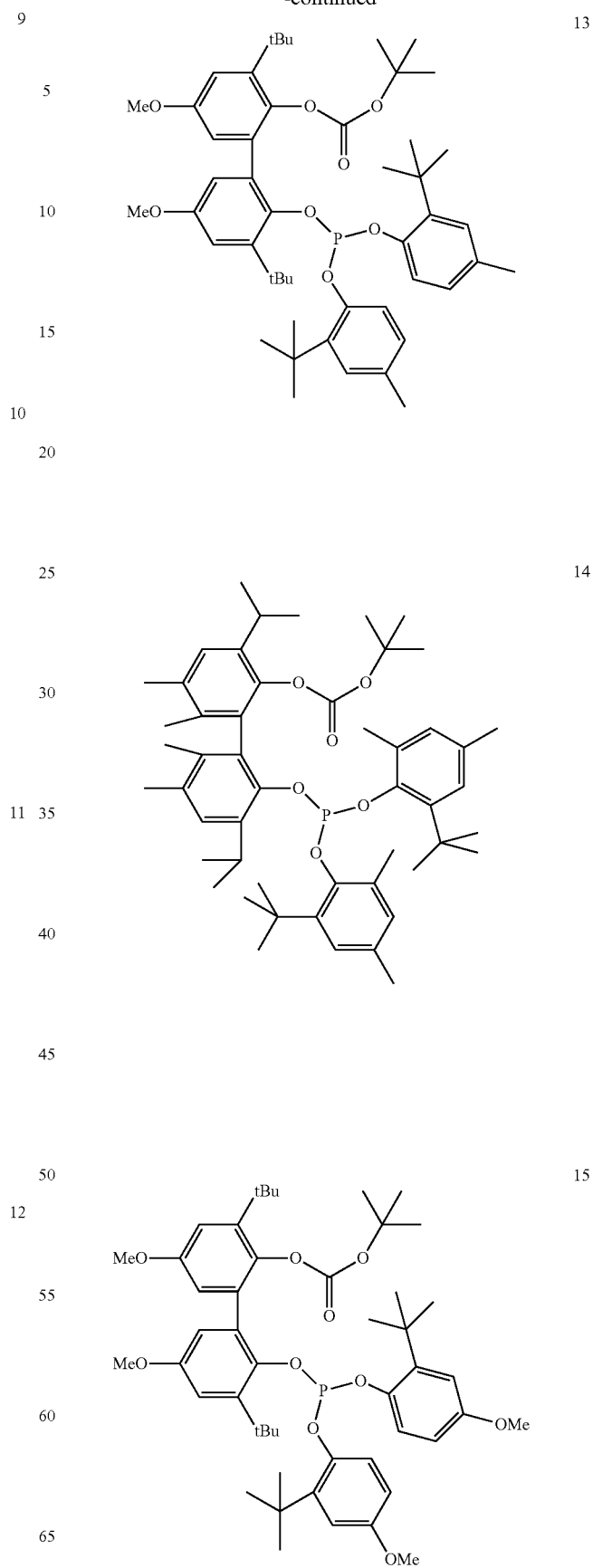

16
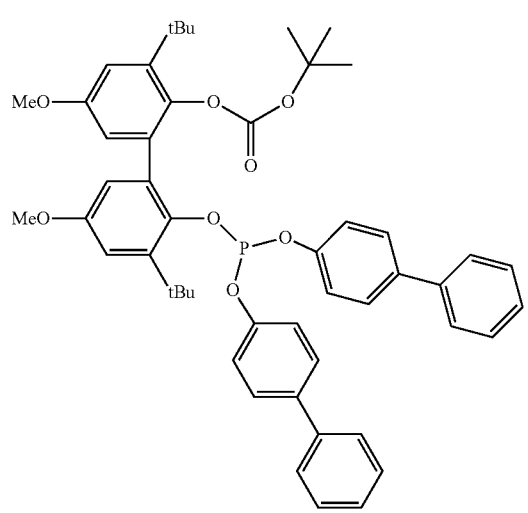
17
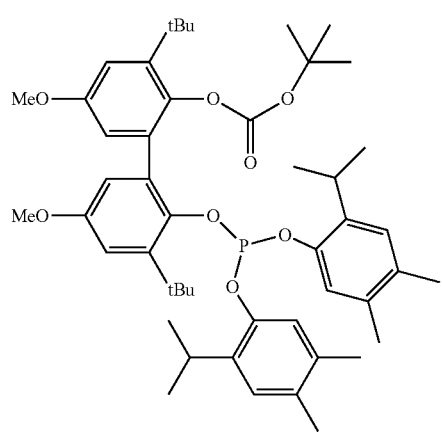
18
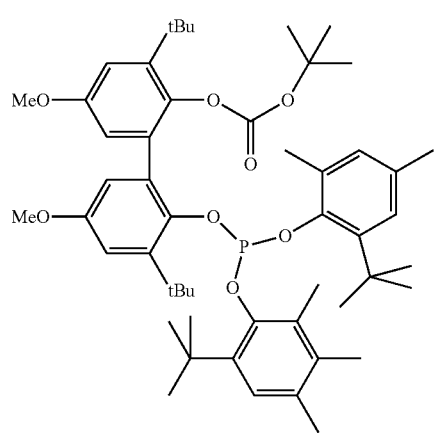
19
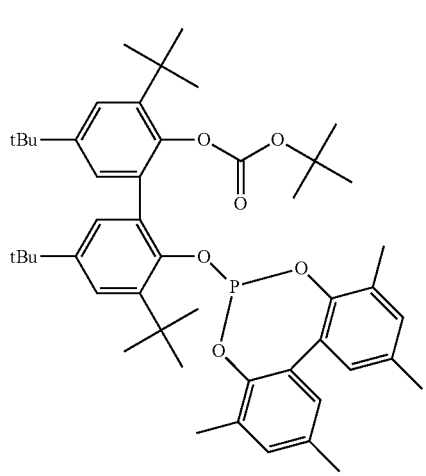
20
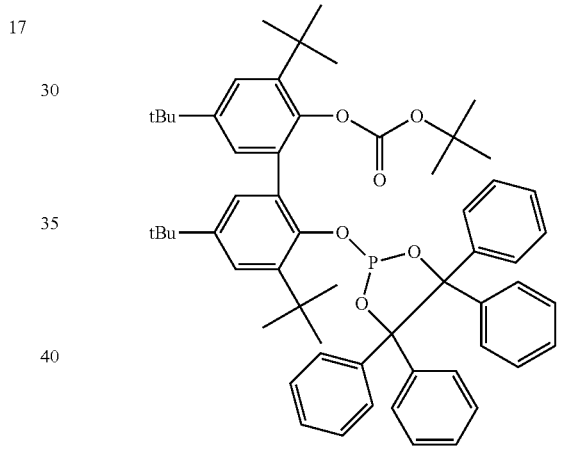
21
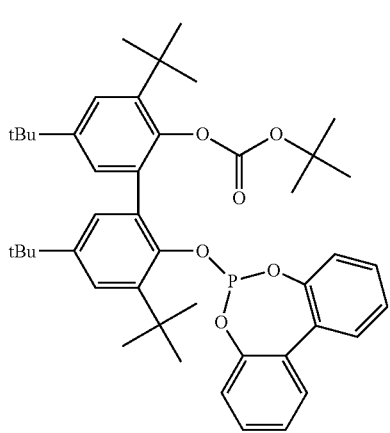

22
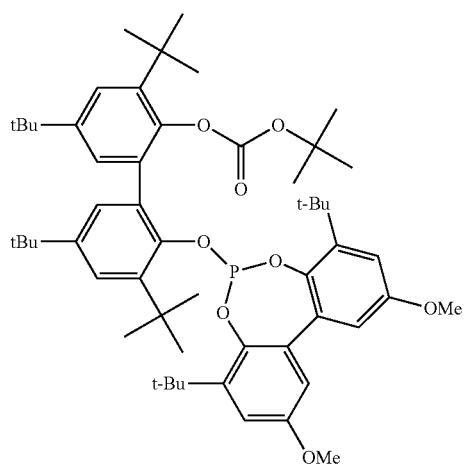
23
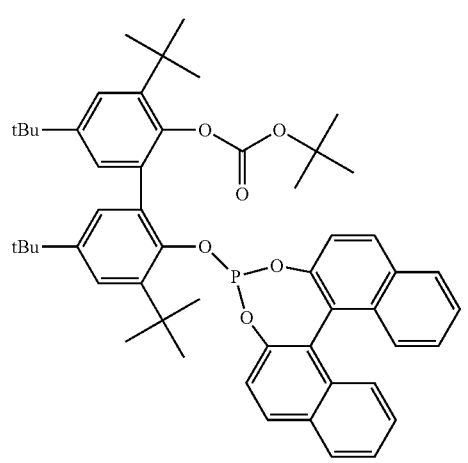
24
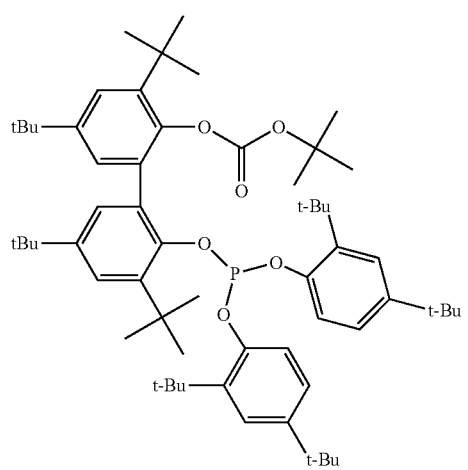
25
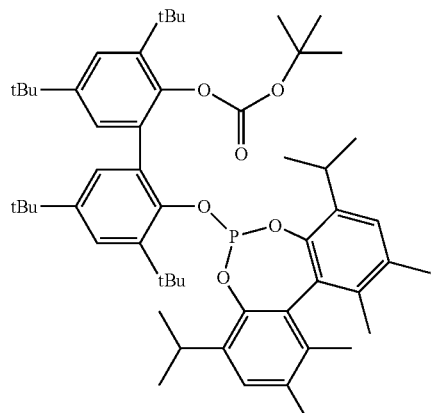
26
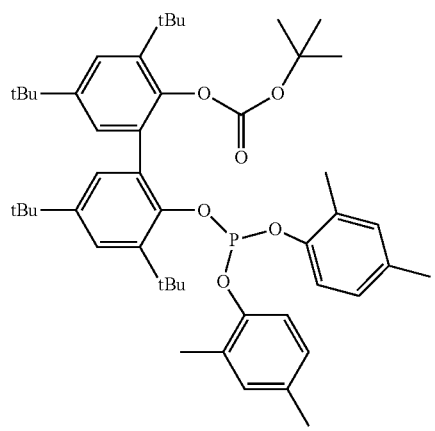
27
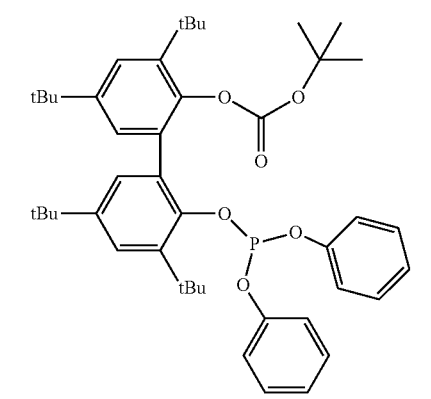
28
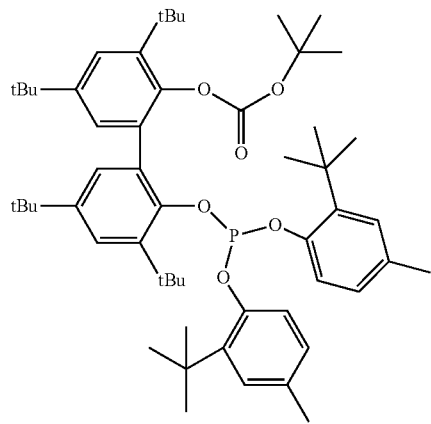

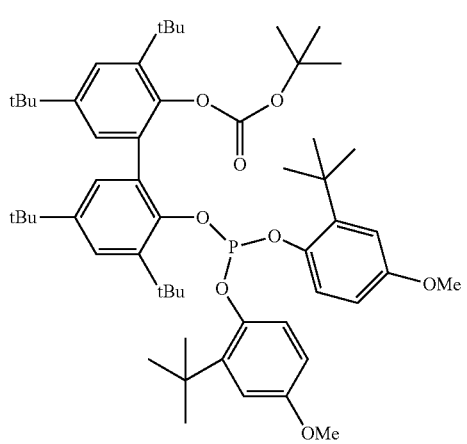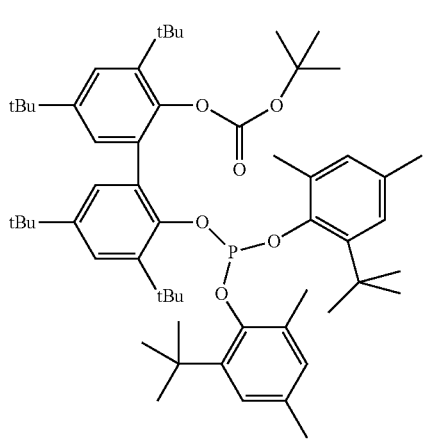

36
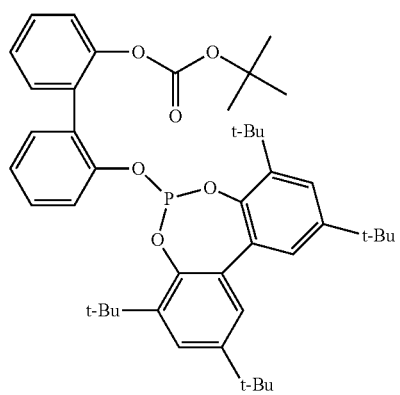
37
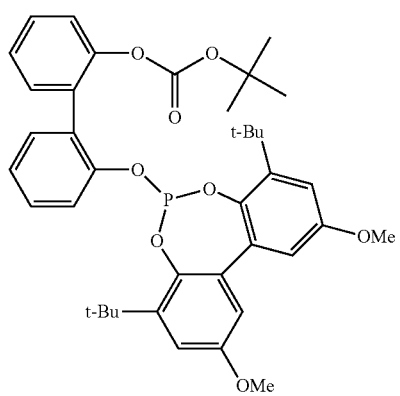
38
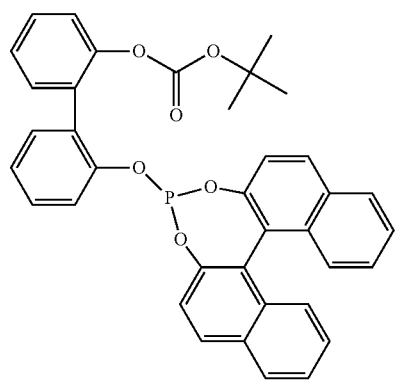
39
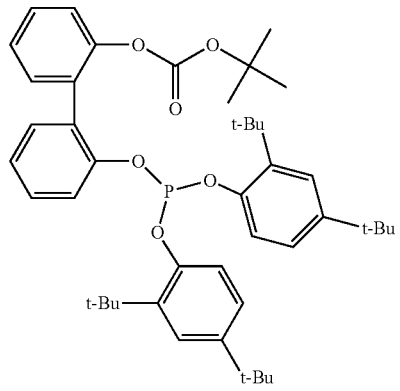
40
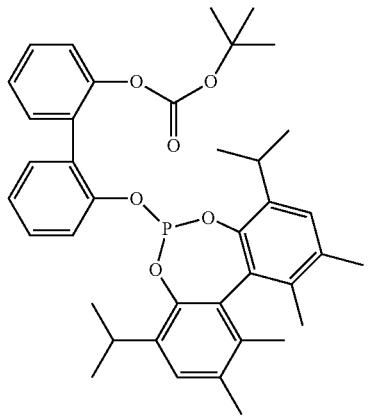
41
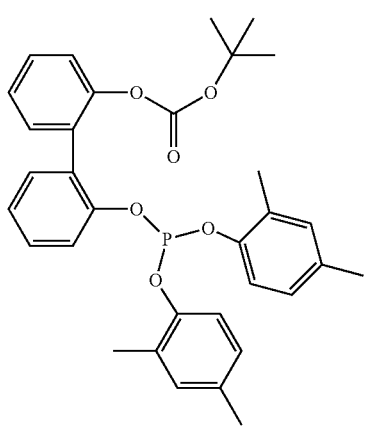
42
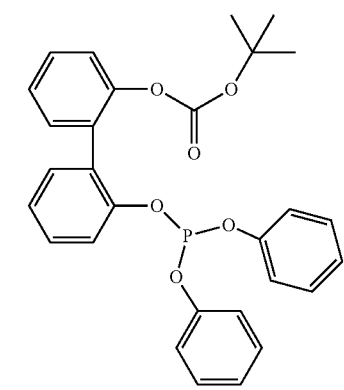
43
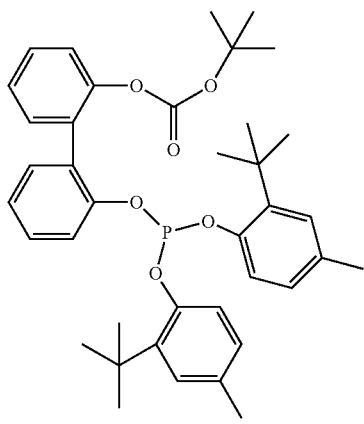

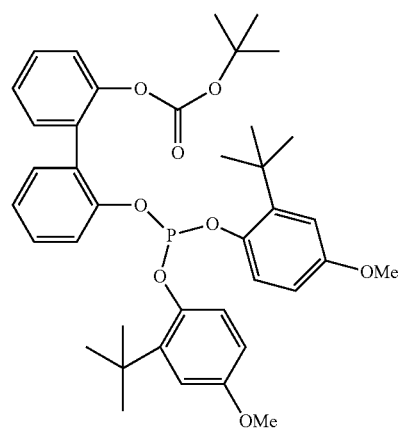
44
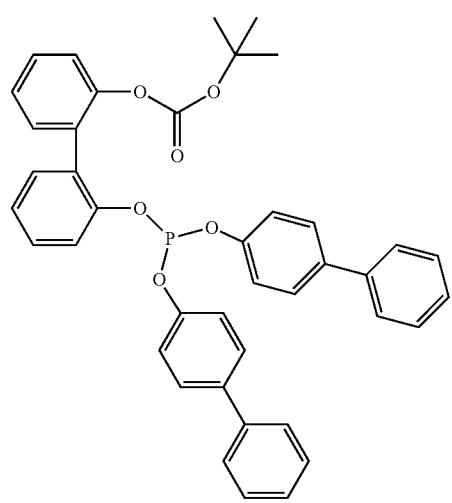
45
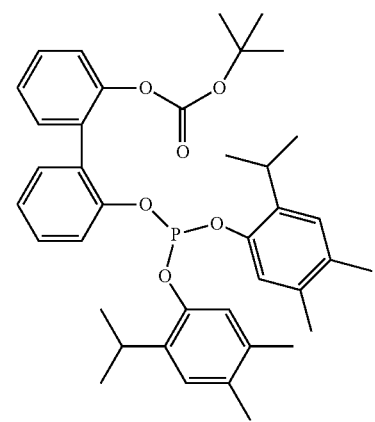
46
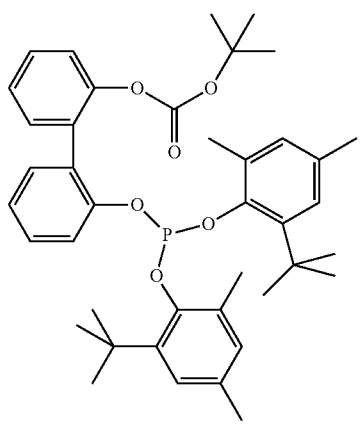
47
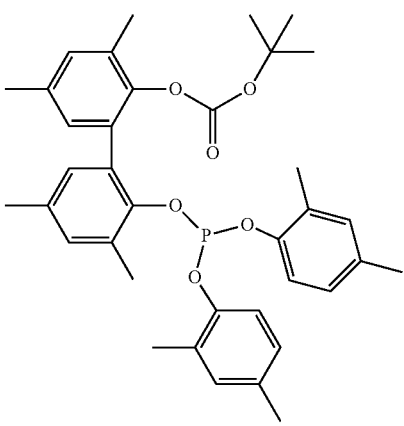
48
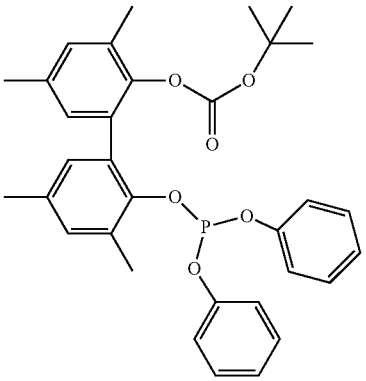
49
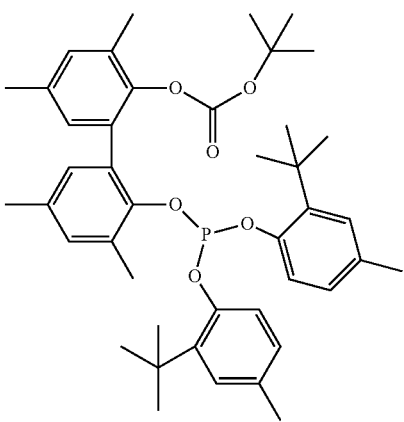
50

51
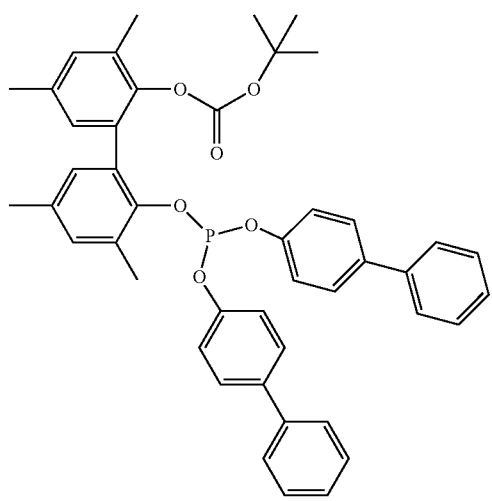
52
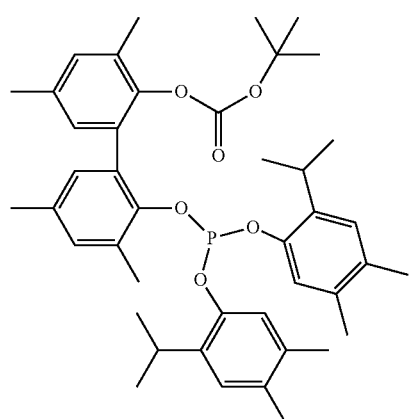
53
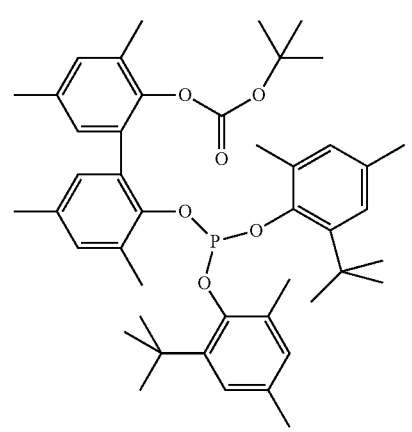
54
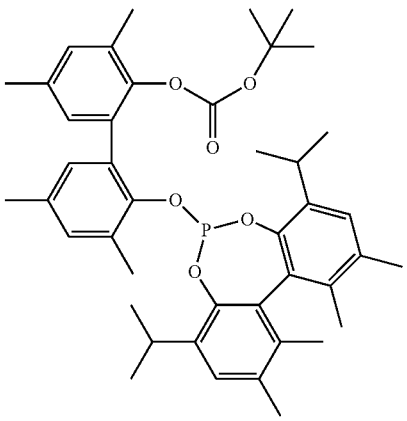
55
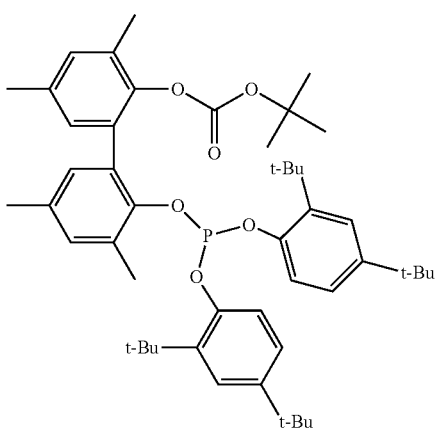
56
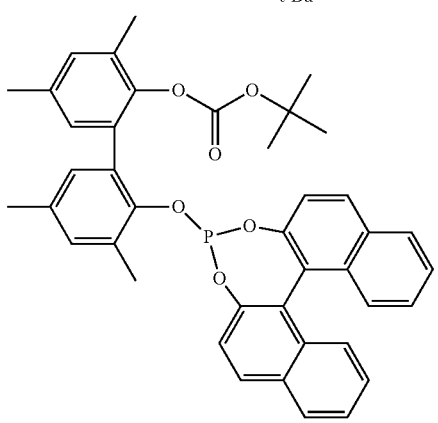
57
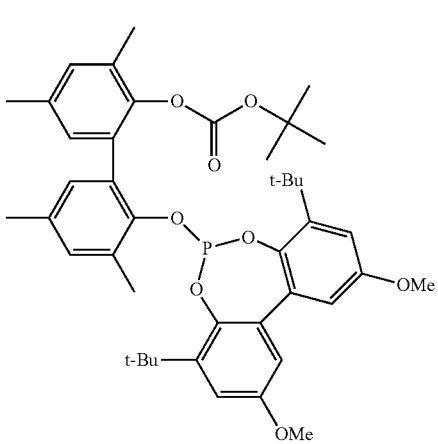

27
-continued
58
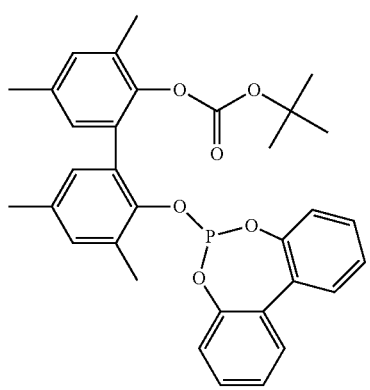
59
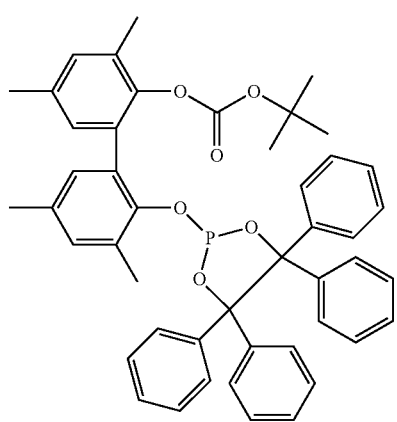
60
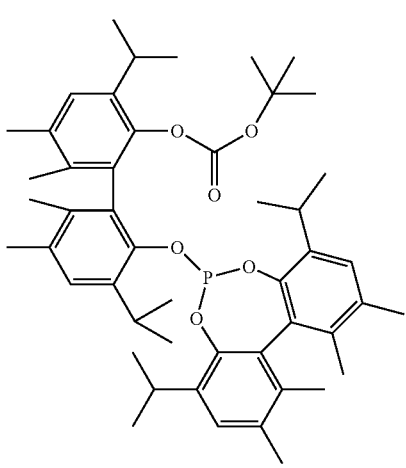
28
-continued
61
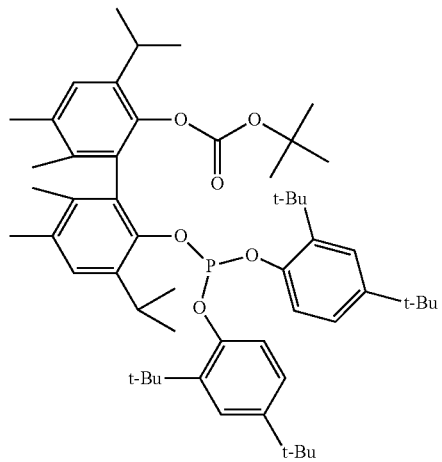
62
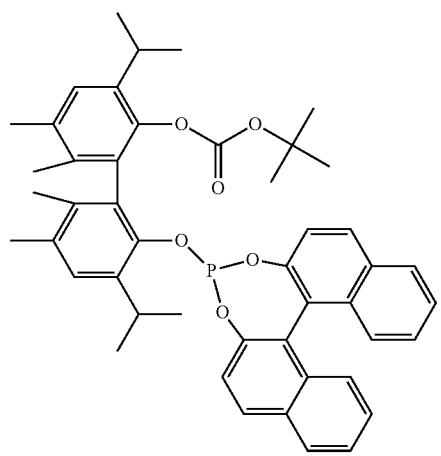
63
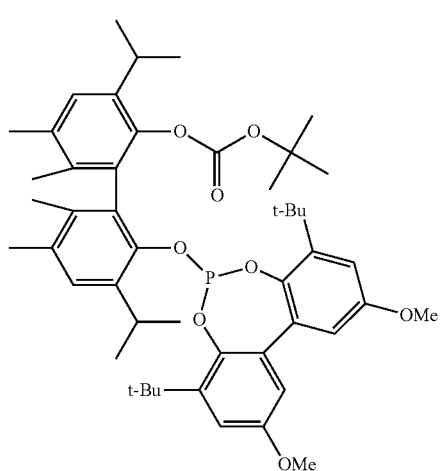

64
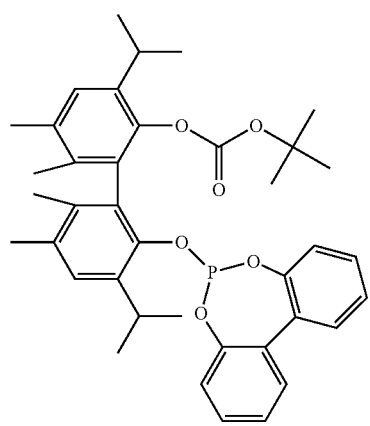
65
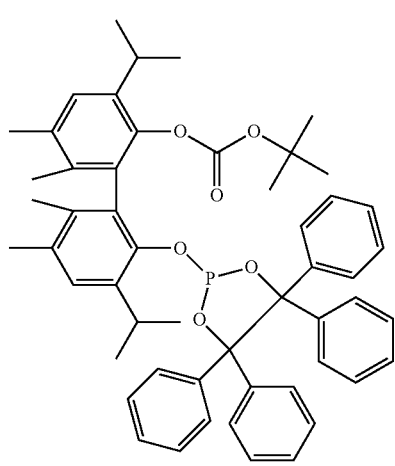
66
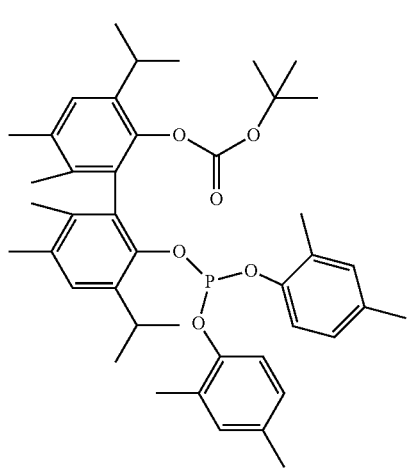
67
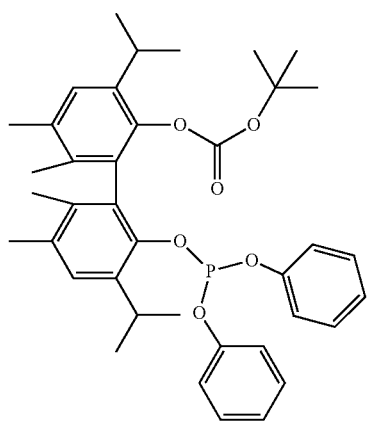
68
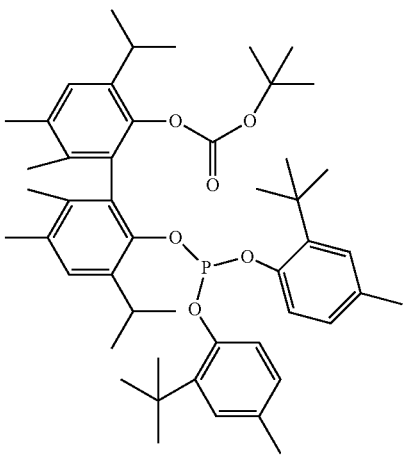
69
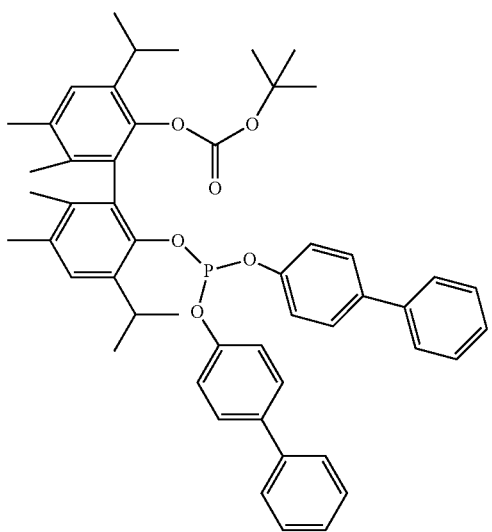

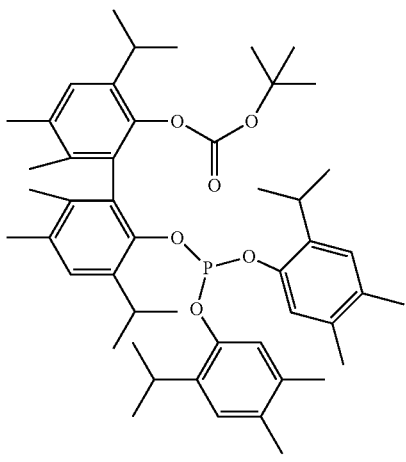

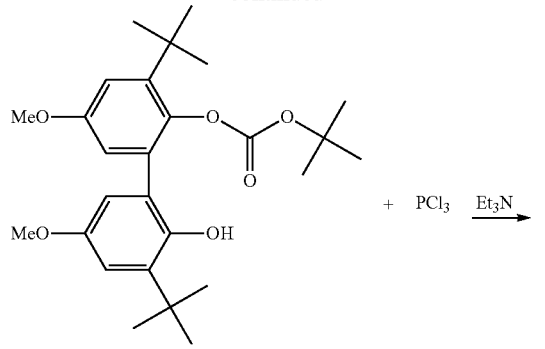

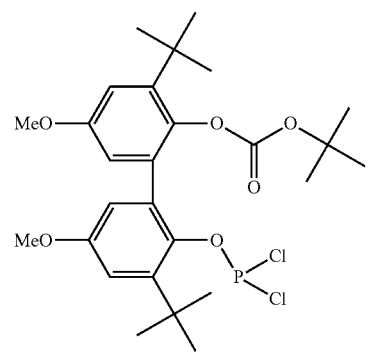

General Operating Procedures

All the preparations which follow were carried out under protective gas using standard Schlenk techniques. The solvents were dried over suitable desiccants before use (Purification of Laboratory Chemicals, W. L. F. Armarego, Christina Chai, Butterworth Heinemann (Elsevier), 6th edition, Oxford 2009).

All preparative operations were effected in baked-out vessels. The products were characterized by means of NMR spectroscopy. Chemical shifts (δ) are reported in ppm. The $^{31}P$ NMR signals were referenced according to: $SR_{31P} = SR_{1H} * (BF_{31P}/BF_{1H}) = SR_{1H} * 0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

Nuclear resonance spectra were recorded by means of a Bruker Avance 300 or Bruker Avance 400; gas chromatography analysis was effected using an Agilent GC 7890A.

The ligands according to the invention can be prepared here in various ways. Three possible ways are shown in the schemes which follow (A to C).

The reaction routes shown are merely illustrative and are shown in highly simplified form. Thus, if required, base can be used additionally in all the steps. In addition, the bases specified in the individual synthesis stages may be replaced by other commercially available bases known to those skilled in the art.

Reaction route A:

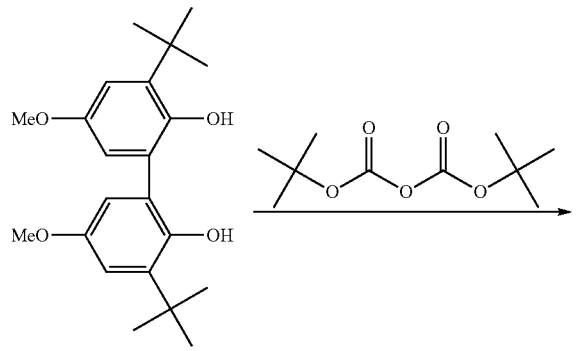

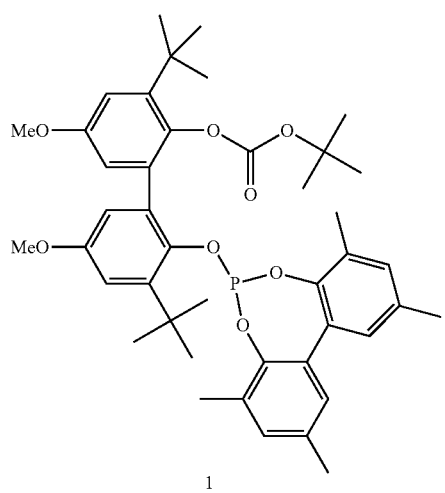

33
-continued
Reaction route B:
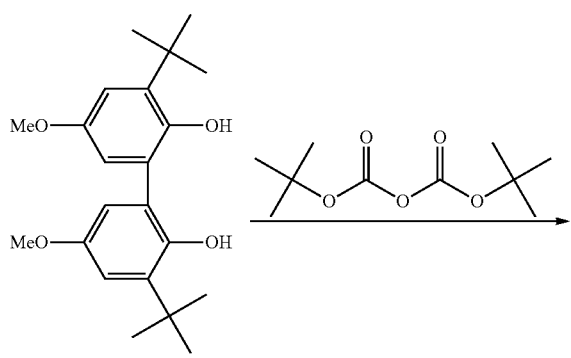
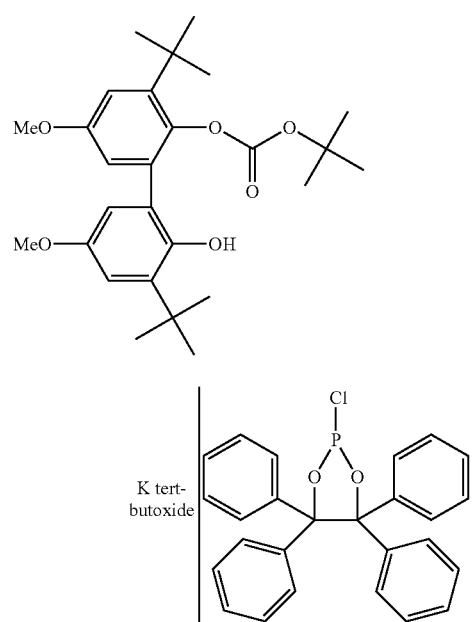
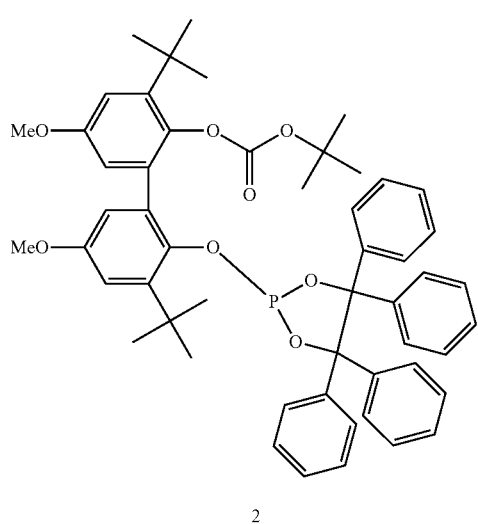
2
34
-continued
Reaction route C:
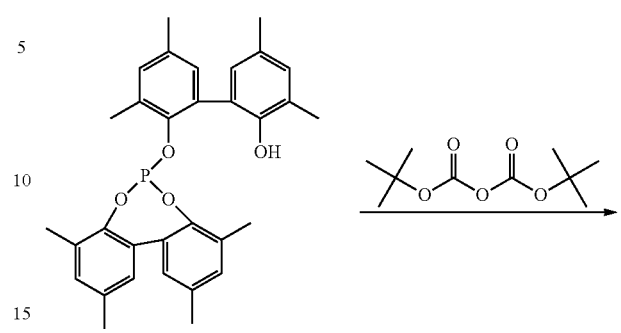
9
Synthesis of Ligand 1
Reaction scheme:
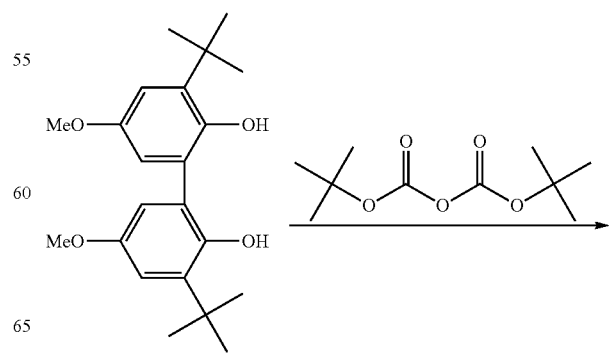

-continued

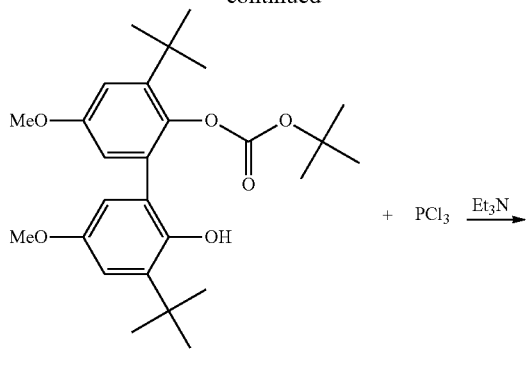

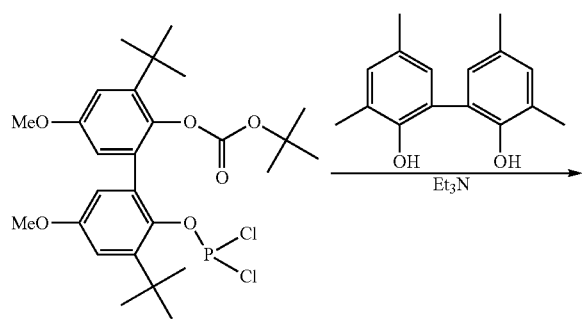

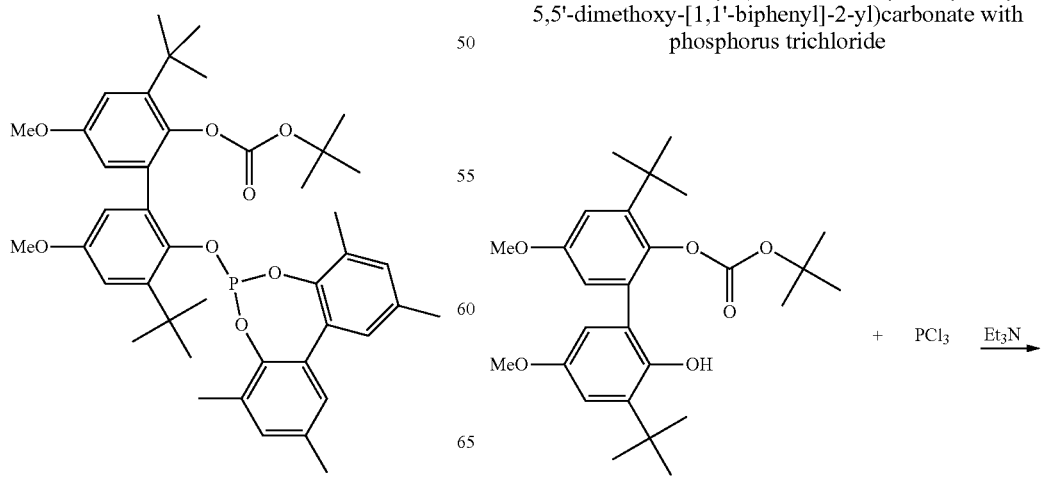

-continued

Introduction of the BOC group:

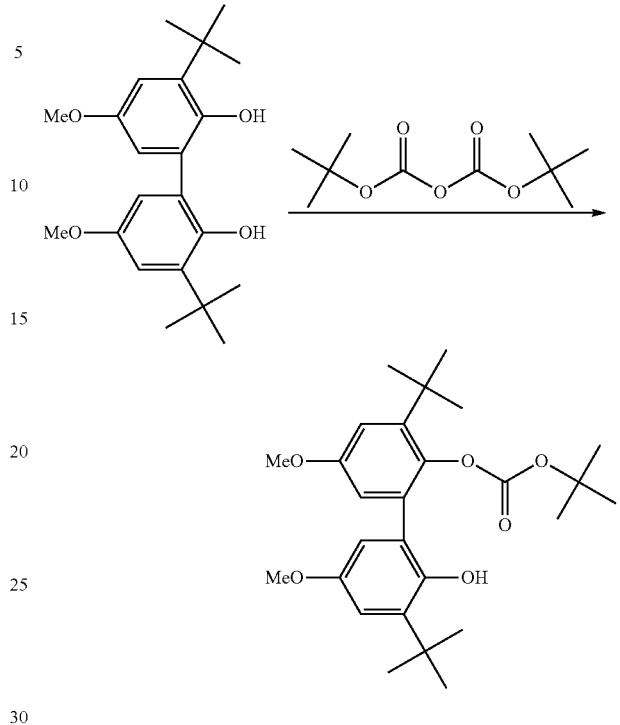

In a 2 l Schlenk flask, 400 mmol (143.8 g) of 3,3'-di-tert-butyl-5,5'-dimethoxy-[1,1'-biphenyl]-2,2'-diol and 40 mmol (4.8 g) of N,N-dimethylaminopyridine (DMAP) were dissolved in 900 ml of $CH_2Cl_2$. Subsequently, at room temperature, 400 mmol (88 g) of di-tert-butyl dicarbonate were dissolved in 280 ml of $CH_2Cl_2$, transferred to a 500 ml dropping funnel and added dropwise to the biphenol/DMAP solution at 32° C. within one hour. The solution was stirred at room temperature overnight. The next morning, the solvent was removed under reduced pressure. The slightly waxy, reddish solid was admixed with 800 ml of n-heptane and stirred overnight. This gave a white residue which was filtered off, washed twice with 50 ml of n-heptane and then dried. The target product was obtained as a white solid (161.6 g, 84%). $^1$H NMR (toluene-d$_8$): 95% and further impurities.

Reaction of tert-butyl (3,3'-di-tert-butyl-2'-hydroxy-5,5'-dimethoxy-[1,1'-biphenyl]-2-yl)carbonate with phosphorus trichloride

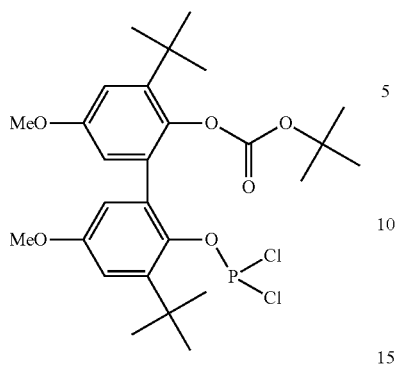

In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to room temperature overnight.

The next morning, the mixture was filtered, the solids were washed with 50 ml of dried toluene, and the filtrate was concentrated to dryness. The target product was obtained as a solid (13.1 g, 89%). $^{31}$P NMR (202.4 MHz, toluene-ds): 203.2 and 203.3 ppm (100%).

Reaction of tert-butyl (3,3'-di-tert-butyl-2'-((dichlorophosphino)oxy)-5,5'-dimethoxy-[1,1'-biphenyl]-2-yl)carbonate with 3,3',5,5'-tetramethyl-(1'-biphenyl)-2,2'-diol

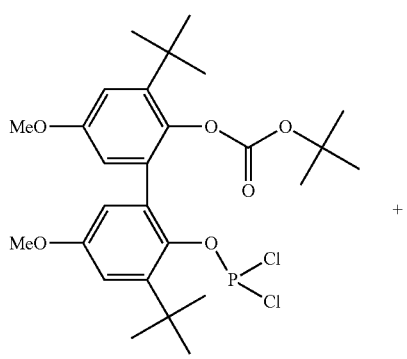

+

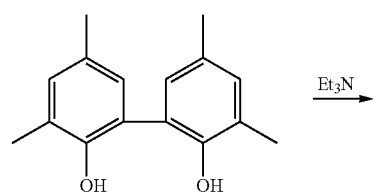

$\xrightarrow{\text{Et}_3\text{N}}$

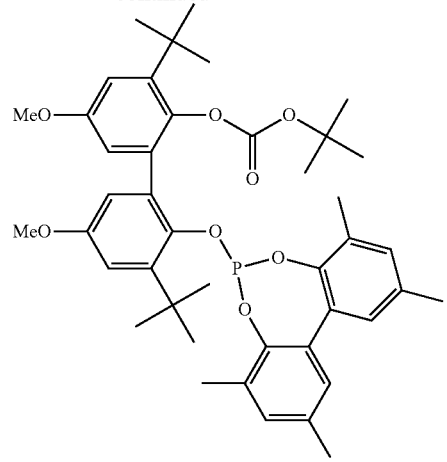

In a 1 l Schlenk flask which had been repeatedly evacuated and filled with inert gas, 24.7 g (0.044 mol) of tert-butyl (3,3'-di-tert-butyl-2'-((dichlorophosphino)oxy)-5,5'-dimethoxy-[1,1'-biphenyl]-2-yl)carbonate were dissolved in 400 ml of acetonitrile.

In a second Schlenk flask (1 l) which had been repeatedly evacuated and filled with inert gas, 10.8 g (0.044 mol) of 3,3',5,5'-tetramethyl-(1,1'-biphenyl)-2,2'-diol were dissolved by stirring in 200 ml of acetonitrile and 13.1 ml (0.011 mol) of dried triethylamine. Subsequently, the chlorophosphite solution was slowly added dropwise to the biphenol-triethylamine solution and the mixture was stirred overnight.

The mixture was then filtered and the residue was washed twice with 15 ml of acetonitrile.

The filtrate was concentrated under reduced pressure until a solid precipitated out. The latter was filtered and dried. The target product was obtained as a white solid (28.5 g, 87%). $^{31}$P NMR (202.4 MHz, toluene-ds): 139.4 ppm (98.5%).

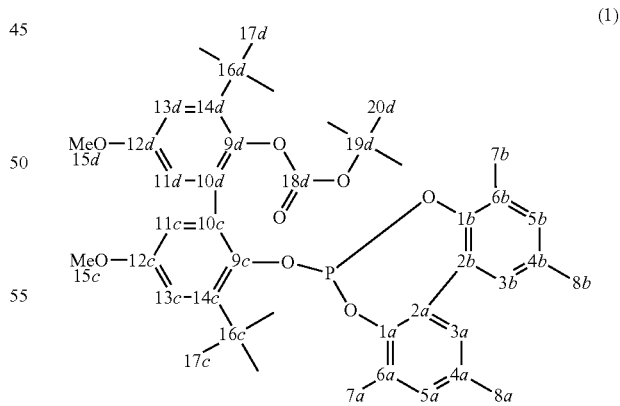

(1)

Spectrometer: Bruker Avance 500 MHz FT spectrometer
Solvent: 1,1,2,2-tetrachloroethane (TCE)
Temperature: 353 K (80° C.)
Referencing: $^1$H NMR, $^{13}$C NMR: TMS=0
$^{31}$P NMR: $SR_{31P} = SR_{1H} * (BF_{31P}/BF_{1H}) = SR_{1H} * 0.404807$

TABLE 1

Assignment of $^1$H chemical shifts of 1

| δ/ppm | Intensity | Multiplicity | Assignment |
|---|---|---|---|
| 1.13 | 9H1 | s | 17d (tert-butyl) |
| 1.20 | 9H | s | 20d (O-tert-butyl) |
| 1.35 | 9H | s | 17c (tert-butyl) |
| 2.02 | 3H | broad s | 7b (methyl) |
| 2.28 | 3H | s | 8b (methyl) |
| 2.31/2.32 | 6H | broad s | 7a (methyl)/8a (methyl) |
| 3.75 | 3H | s | 15c (O-methyl) |
| 3.78 | 3H | s | 15d (O-methyl) |
| 6.68 | 1H | d | 11d |
| 6.83 | 1H | d | 11c |
| 6.88 | 2H (1 + 1) | m | 5b, 13d |
| 6.94 | 1H | d | 13c |
| 6.96 | 1H | s | 5a |
| 6.99 | 2H (1 + 1) | s | 3a + 3b | s: singlet
d: doublet
t: triplet
q: quartet
m: multiplet

TABLE 2

Assignment of $^{13}$C chemical shifts of 1

| δ/ppm | Intensity | Group | Assignment |
|---|---|---|---|
| 16.35 | 1 | $CH_3$ | 7b |
| 16.61 | 1 | $CH_3$ | 7a |
| 20.66 | 1 | $CH_3$ | 8b |
| 20.71 | 1 | $CH_3$ | 8a |
| 27.38 | 3 | $CH_3$ | 20d |
| 30.27 | 3 | $CH_3$ | 17d |
| 30.41 | 3 | $CH_3$ | 17c |
| 34.85 | 1 | $C_q$ | 16c |
| 35.02 | 1 | $C_q$ | 16d |
| 55.67 | 1 | $CH_3$ | 15d |
| 55.79 | 1 | $CH_3$ | 15c |
| 81.67 | 1 | $C_q$ | 19d |
| 113.86 | 1 | CH | 11c |
| 114.01 | 1 | CH | 11d |
| 114.14 | 1 | CH | 13c |
| 114.60 | 1 | CH | 13d |
| 127.65 | 1 | CH | 3b |
| 127.88 | 1 | CH | 3a |
| 128.72 | 1 | $C_q$ | 10d |
| 130.01 | 1 | $C_q$ | 6b |
| 130.77 | 1 | $C_q$ | 6a |
| 130.86 | 1 | CH | 5b |
| 130.92 | 1 | CH | 5a |
| 131.37 | 1 | $C_q$ | 2b |
| 131.50 | 1 | $C_q$ | 2a |
| 133.49 | 1 | $C_q$ | 4b |
| 133.65 | 1 | $C_q$ | 4a |
| 135.68 | 1 | $C_q$ | 10c |
| 142.09 | 1 | $C_q$ | 9d |
| 142.37 | 1 | $C_q$ | 14d |
| 143.60 | 1 | $C_q$ | 9c |
| 144.05 | 1 | $C_q$ | 14c |
| 145.88 | 1 | $C_q$ | 1b |
| 146.00 | 1 | $C_q$ | 1a |
| 151.27 | 1 | $C_q$ | 18d |
| 154.18 | 1 | $C_q$ | 12d |
| 157.19 | 1 | $C_q$ | 12c |

Synthesis of Ligand 2

Reaction of tert-butyl (3,3'-di-tert-butyl-2'-hydroxy-5,5'-dimethoxy-[1,1'-biphenyl]-2-yl)carbonate with 2-chloro-4,4,5,5-tetraphenyl-1,3,2-dioxaphospholane

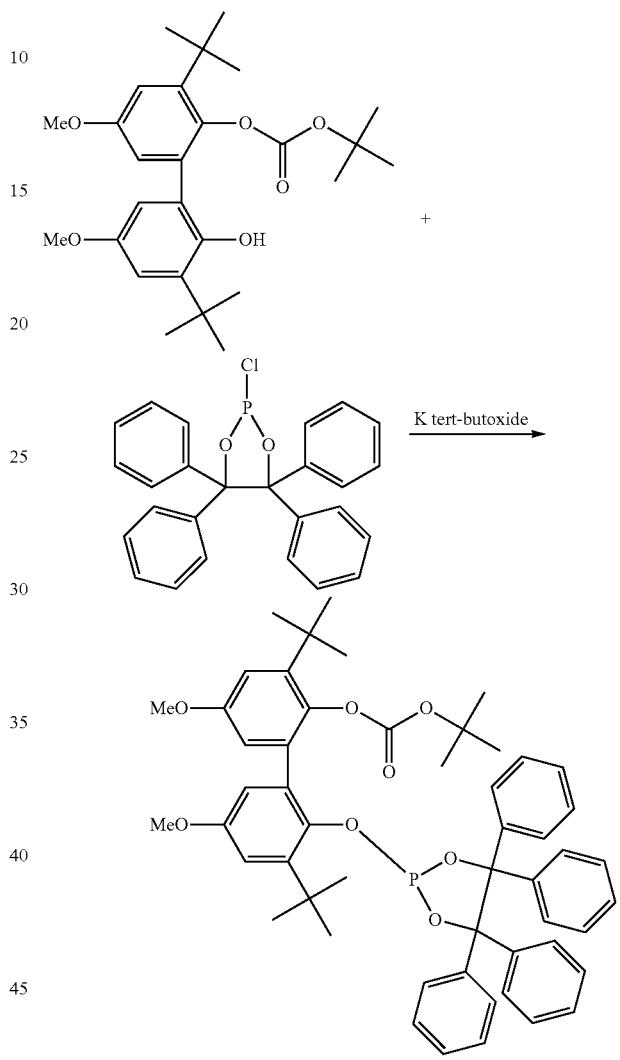

In a 250 ml Schlenk flask which had been repeatedly evacuated and filled with inert gas, 9.1 g (0.021 mol) of 2-chloro-4,4,5,5-tetraphenyl-1,3,2-dioxaphospholane were dissolved in 75 ml of dried toluene.

In a second Schlenk flask (250 ml), 9.2 g (0.02 mol) of tert-butyl (3,3'-di-tert-butyl-2'-hydroxy-5,5'-dimethoxy-[1,1'-biphenyl]-2-yl)carbonate and 2.3 g (0.02 mol) of potassium tert-butoxide were dissolved in 75 ml of dried toluene while stirring.

Subsequently, the carbonate/potassium tert-butoxide/toluene mixture was slowly added dropwise at room temperature to the chlorophosphite solution, and the mixture was stirred at room temperature overnight.

Thereafter, the solvent was removed under reduced pressure. The resultant residue was stirred in 75 ml of dried acetonitrile for 5 hours. The solids were filtered, washed with dried acetonitrile and dried. The target product was obtained as a white solid (15.3 g, 90%). $^{31}$P NMR (202.4 MHz, toluene-d8): 147.0 ppm (99%).

(2)

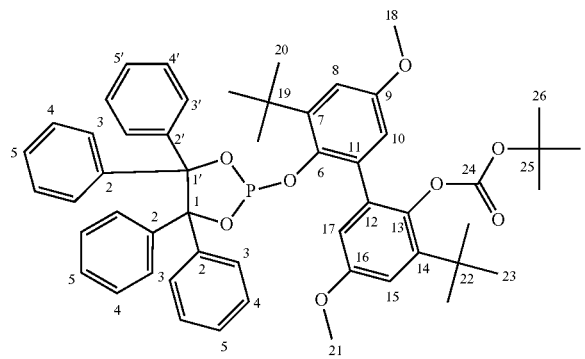

Referencing:

$^1$H NMR: TMS=0 ppm, $^{31}$P NMR: $SR_{31P}=SR_{1H}*(BF_{31P}/BF_{1H})=SR_{1H}*0.404807$

TABLE 3

Assignment of the $^{13}$C chemical shifts of 2

| δ [ppm] | Intensity | Group | Assignment |
|---|---|---|---|
| 157.31 | 1 × C | $C_q$ | C9 |
| 155.29 | 1 × C | $C_q$ | C16 |
| 152.22 | 1 × C | $C_q$ | C24 |
| 143.68 | 1 × C | $C_q$ | C13 |
| 143.66/143.54 | 2 × C | $C_q$ | C7, C14 |
| 143.35 | 1 × C | $C_q$ | C6 |
| 142.99/142.80 142.72/142.49 | 4 × C | $C_q$ | C2 |
| 135.65 | 1 × C | $C_q$ | C11 |
| 132.78 | 1 × C | $C_q$ | C12 |
| 131.30/130.45 129.66/129.04 | 8 × C | CH | C4 |
| 127.40-126.90 | 12 × C | CH | C3, C5 |
| 115.17 | 1 × C | CH | C10 |
| 114.89 | 1 × C | CH | C8 |
| 114.83 | 1 × C | CH | C15 |
| 114.10 | 1 × C | CH | C17 |
| 95.64/94.85 | 2 × C | $C_q$ | C1, C1' |
| 81.32 | 1 × C | $C_q$ | C25 |
| 55.08 | 1 × C | $CH_3$ | C21 |
| 55.04 | 1 × C | $CH_3$ | C18 |
| 35.25 | 1 × C | $C_q$ | C19 |
| 35.09 | 1 × C | $C_q$ | C22 |
| 30.77 | 3 × C | $CH_3$ | C20 |
| 30.64 | 3 × C | $CH_3$ | C23 |
| 27.56 | 3 × C | $CH_3$ | C26 |

TABLE 4

Assignment of the $^1$H chemical shifts of 2

| δ [ppm] | Intensity | Group | Assignment |
|---|---|---|---|
| 7.54 | 4H | m | H3, H4, H5 |
| 7.21 | 3H | m | H8, H10 |
| 7.09 | 5H | m | H15, H17 |
| 6.99-6.89 | 6H | m | |
| 6.83 | 6H | m | |
| 3.50 | 3H | s | H19 |
| 3.41 | 3H | s | H22 |
| 1.39 | 9H | s | H20 |
| 1.31 | 9H | s | H23 |
| 1.21 | 9H | s | H26 |

Synthesis of Ligand 3

Reaction of tert-butyl (3,3'-di-tert-butyl-2'-((dichlorophosphino)oxy)-5,5'-dimethoxy-[1,1'-biphenyl]-2-yl)carbonate with 2,2'-biphenol

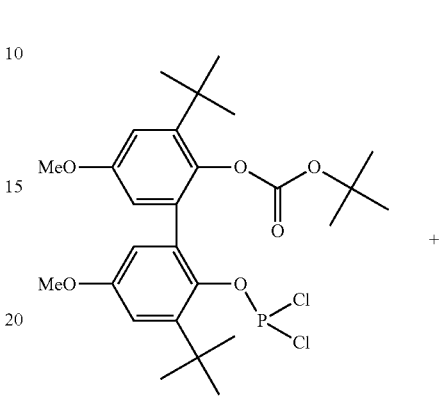

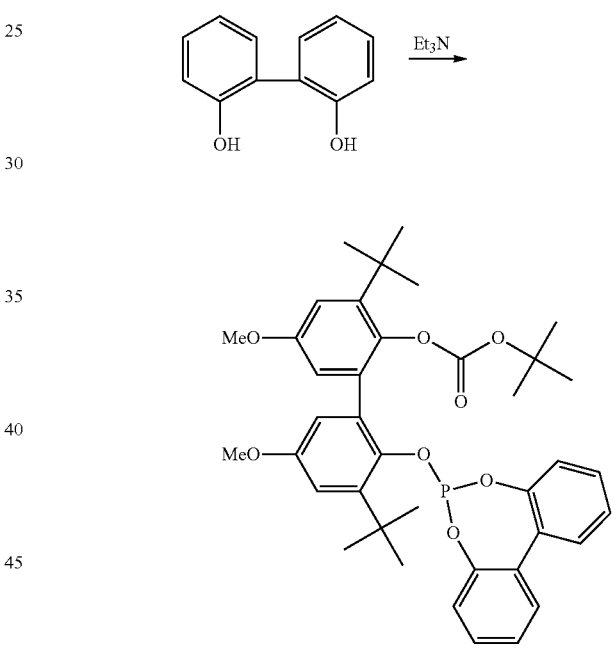

In a 250 ml Schlenk flask which had been repeatedly evacuated and filled with inert gas, 10.5 g (0.019 mol) of tert-butyl (3,3'-di-tert-butyl-2'-((dichlorophosphino)oxy)-5,5'-dimethoxy-[1,1'-biphenyl]-2-yl)carbonate were dissolved in 50 ml of degassed acetonitrile while stirring.

In a second Schlenk flask (250 ml) which had been repeatedly evacuated and filled with inert gas, 3.6 g (0.019 mol) of 2,2'-biphenol were dissolved in 40 ml of degassed acetonitrile and 6.3 ml (0.045 mol) of dried triethylamine while stirring. Subsequently, the chlorophosphite mixture was slowly added dropwise at room temperature to the biphenol/triethylamine solution, and the mixture was stirred at room temperature overnight. The resultant solids were filtered and dried. The target product was obtained as a white solid (11.5 g, 90%). $^{31}$P NMR (202.4 MHz, toluene-d$_6$): 146.2 ppm (100%).

(3)

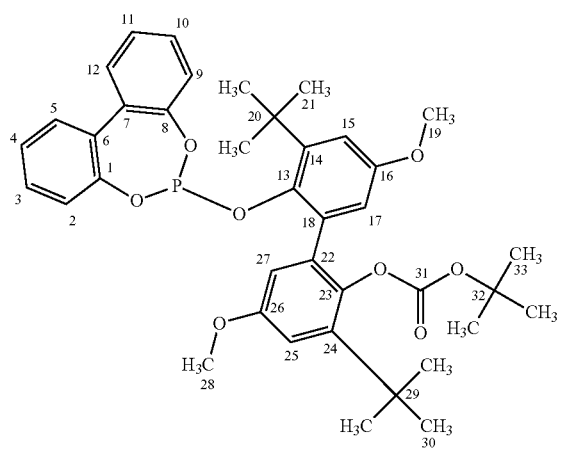

TABLE 5

Assignment of the $^{13}C$ chemical shifts of 3

| δ [ppm] | Intensity | Group | Assignment |
|---|---|---|---|
| 157.46 | 1 × C | $C_q$ | C16 |
| 155.51 | 1 × C | $C_q$ | C26 |
| 151.76 | 1 × C | $C_q$ | C31 |
| 150.51/149.92 | each 1 × C | $C_q$ | C1 + C8 |
| 144.07 | 1 × C | $C_q$ | C24 |
| 143.62 | 1 × C | $C_q$ | C13 |
| 142.70 | 1 × C | $C_q$ | C23 |
| 142.67 | 1 × C | $C_q$ | C14 |
| 135.75 | 1 × C | $C_q$ | C18 |
| 132.13/131.73 | 1 × C | $C_q$ | C6 + C7 |
| 131.30 | 1 × C | $C_q$ | C22 |
| 129.87/128.94 | each 1 × C | CH | C5 + C12 |
| 128.98/128.91 | each 1 × C | CH | C3 + C10 |
| 125.16/124.98 | each 1 × C | CH | C4 + C11 |
| 123.54/122.40 | each 1 × C | CH | C2 + C9 |
| 115.14 | 1 × C | CH | C25 |
| 114.93 | 1 × C | CH | C15 |
| 114.85 | 1 × C | CH | C27 |
| 114.72 | 1 × C | CH | C17 |
| 81.36 | 1 × C | $C_q$ | C32 |
| 55.14 | 1 × C | $CH_3$ | C28 |
| 55.10 | 1 × C | $CH_3$ | C19 |
| 35.57 | 1 × C | $C_q$ | C29 |
| 35.22 | 1 × C | $C_q$ | C20 |
| 30.78 | 3 × C | $CH_3$ | C30 |
| 30.62 | 3 × C | $CH_3$ | C21 |
| 27.45 | 3 × C | $CH_3$ | C33 |

TABLE 6

Assignment of the $^1H$ chemical shifts of 3

| δ [ppm] | Intensity | Group | Assignment |
|---|---|---|---|
| 7.26 | 1H | d (J = 7.7 Hz) | H2, H9, H3, H10 |
| 7.15-7.09 | 6H | m | H5, H12, H15, H25 |
| 7.02 | 1H | t (J = 7.7 Hz) | |
| 6.95/6.91 | 2 × 1H | 2 × t (J ~ 7.5 Hz) | H4/H11 |
| 6.93 | 1H | d (J = 3 Hz) | H17 |
| 6.87 | 1H | d (J = 3 Hz) | H27 |
| 3.48 | 3H | s | H19 |
| 3.42 | 3H | s | H29 |
| 1.50 | 9H | s | H20 |
| 1.35 | 9H | s | H21 |
| 1.16 | 9H | s | H33 |

Synthesis of Ligand 4

Reaction of tert-butyl (3,3'-di-tert-butyl-2'-((dichlorophosphino)oxy)-5,5'-dimethoxy-[1,1'-biphenyl]-2-yl)carbonate with 3,3,5,5-tetra-tert-butylbiphenol

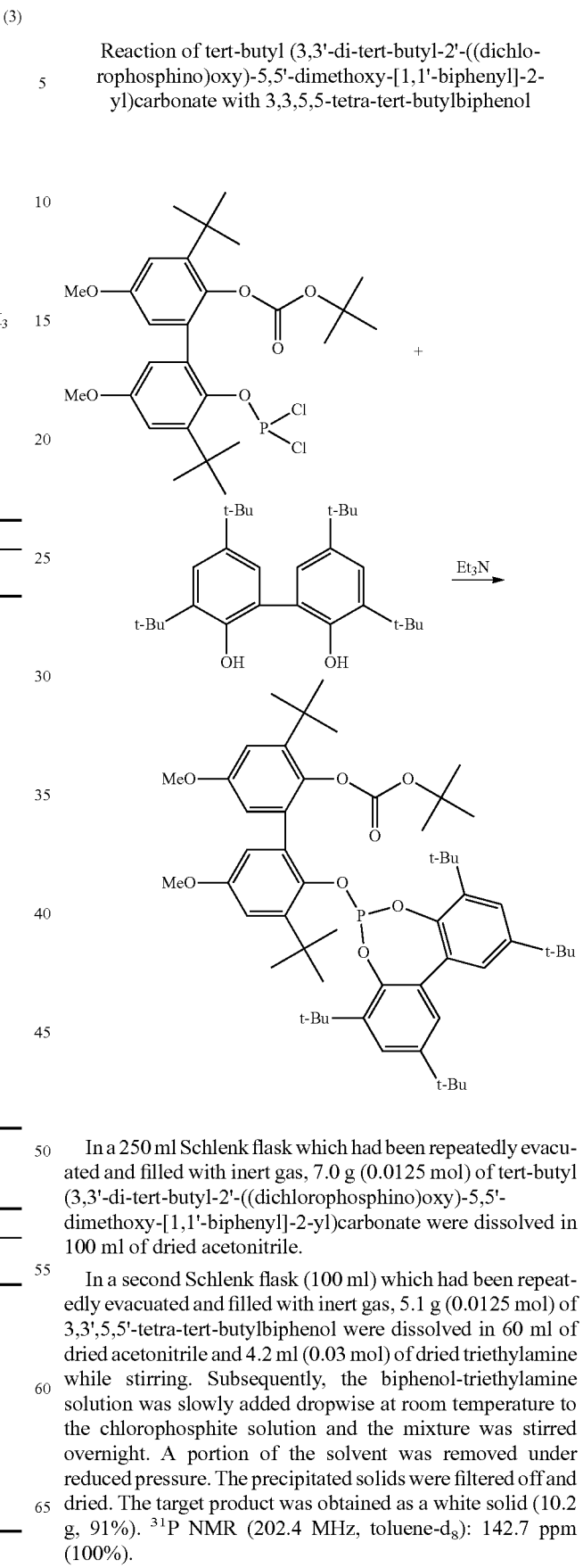

In a 250 ml Schlenk flask which had been repeatedly evacuated and filled with inert gas, 7.0 g (0.0125 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 5.1 g (0.0125 mol) of 3,3',5,5'-tetra-tert-butylbiphenol were dissolved in 60 ml of dried acetonitrile and 4.2 ml (0.03 mol) of dried triethylamine while stirring. Subsequently, the biphenol-triethylamine solution was slowly added dropwise at room temperature to the chlorophosphite solution and the mixture was stirred overnight. A portion of the solvent was removed under reduced pressure. The precipitated solids were filtered off and dried. The target product was obtained as a white solid (10.2 g, 91%). $^{31}P$ NMR (202.4 MHz, toluene-$d_8$): 142.7 ppm (100%).

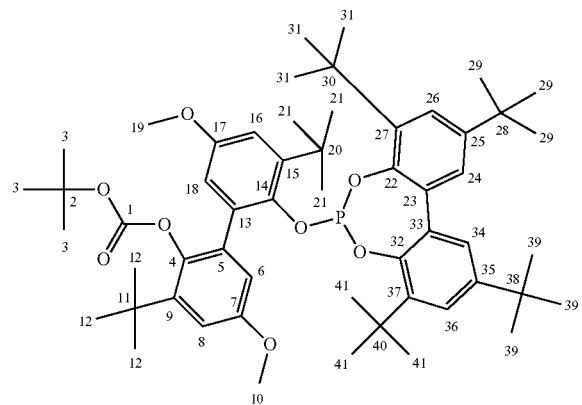 [SMILES: COc1cc(-c2cc(OC)cc(C(C)(C)C)c2Op2oc3c(C(C)(C)C)cc(C(C)(C)C)cc3c3cc(C(C)(C)C)cc(C(C)(C)C)c3o2)c(OC(=O)OC(C)(C)C)c(C(C)(C)C)c1]

TABLE 7

| Assignment of the chemical shifts of 4 | | |
| --- | --- | --- |
| Number | δ-¹H/ppm | δ-¹³C/ppm |
| 1 | — | 151.6 |
| 2 | — | 81.5 |
| 3 | 1.18 | 27.3 |
| 4 | — | 142.3 |
| 5 | — | 129.9 |
| 6\|18 | 6.76 | 114.7 |
|  | 6.67 | 114.1 |
| 7\|17 | — | 154.4 |
|  |  | 156.8 |
| 8\|16 | 6.93 | 113.5 |
|  | 6.88 | 115.4 |
| 9 | — | 143.6 |
| 10\|19 | 3.78 | 55.4 |
|  | 3.74 | 55.7 |
| 11 | — | 35.0 |
| 12 | 1.39 | 30.6 |
| 21\|29\|31\|39\|41 | 1.03 | 31.2 |
|  | 1.24 | 31.0 |
|  | 1.29 | 31.4 |
|  | 1.34 | 31.5 |
|  | 1.39 | 30.7 |
|  | 1.48 | 31.3 |
| 13 | — | 136.4 |
| 14 | — | 142.1 |
| 15 | — | 140.1 |
| 20 | — | 34.6 |
| 22\|32 | — | 146.0 |
|  |  | 146.9 |
| 24\|34 | 7.06 | 126.6 |
|  | 7.30 | 123.8 |
| 25\|35 | — | 145.1 |
|  |  | 146.3 |
| 26\|36 | 7.08 | 126.3 |
|  | 7.42 | 124.1 |
| 28\|38 | — | 35.1 |
|  |  | 35.2 |
| 30\|40 | — | 34.6 |
|  |  | 35.4 |
| 23\|33 | — | 135.5 |
|  |  | 132.6 |
| 27\|37 | — | 140.0 |
|  |  | 141.9 |

Synthesis of Ligand 5

Reaction of tert-butyl (3,3'-di-tert-butyl-2'-((dichlorophosphino)oxy)-5,5'-dimethoxy-[1,1'-biphenyl]-2-yl)carbonate with 3,3-di-tert-butyl-5,5-dimethoxybiphenol

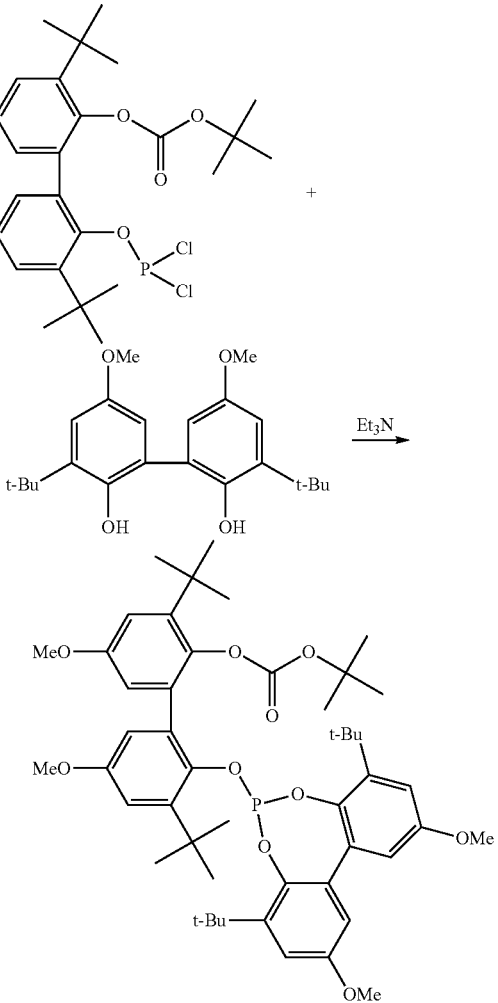

In a 250 ml Schlenk flask which had been repeatedly evacuated and filled with inert gas, 7 g (0.0125 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 4.5 g (0.0125 mol) of 3,3-di-tert-butyl-5,5-dimethoxybiphenol were dissolved in 60 ml of dried acetonitrile and 4.2 ml (0.03 mol) of degassed triethylamine. Subsequently, the biphenol-triethylamine solution was slowly added dropwise at room temperature to the chlorophosphite solution and the mixture was stirred at room temperature overnight.

A portion of the solvent was removed under reduced pressure. The precipitated solids were filtered off and dried. The target product was obtained as a white solid (10.5 g, 96%). ³¹P NMR (202.4 MHz, toluene-ds): 140.9 (95.2%) and further impurities (further impurities=P—H compounds, oxide compounds, as yet incompletely converted chlorophosphite).

Synthesis of Ligand 11

Reaction of tert-butyl (3,3'-di-tert-butyl-2'-((dichlorophosphino)oxy)-5,5'-dimethoxy-[1,1'-biphenyl]-2-yl)carbonate with 2,4-dimethylphenol

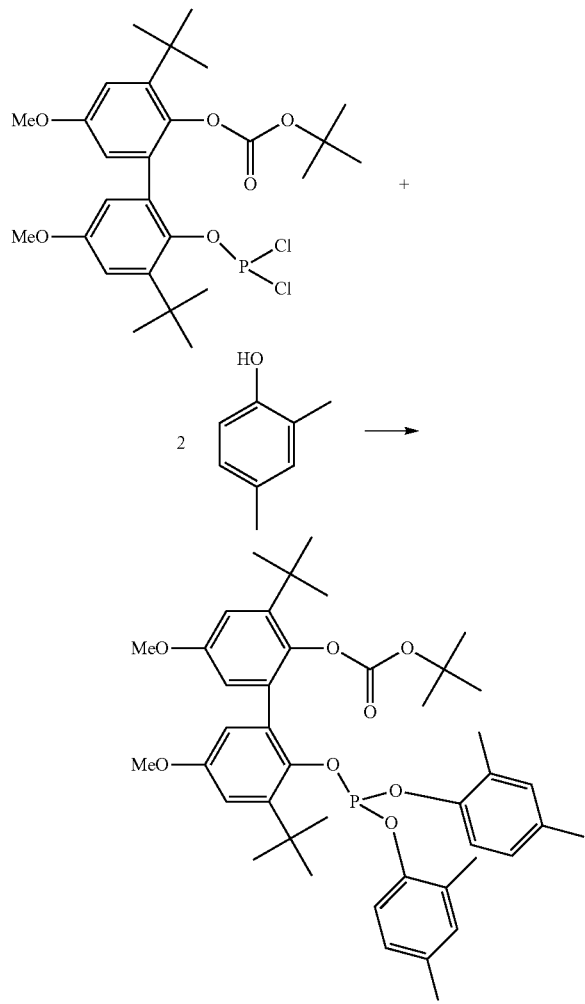

In a 500 ml Schlenk flask which had been repeatedly evacuated and filled with inert gas, 6.8 g (0.012 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (250 ml) which had been repeatedly evacuated and filled with inert gas, 6 g (6 ml; 0.048 mol) of 2,4-dimethylphenol were dissolved in 100 ml of dried acetonitrile and 5 g (7 ml; 0.059 mol) of degassed triethylamine. Subsequently, the biphenol-triethylamine solution was slowly added dropwise at room temperature to the chlorophosphite solution and the mixture was stirred at room temperature overnight and cooled in an ice bath the next morning.

A portion of the solvent was removed under reduced pressure. This formed a slime-like solution which solidified after prolonged drying. The target product was obtained as a white solid (11.8 g, 62%). $^{31}$P NMR (202.4 MHz, toluene-d$_8$): 139.1 (92.8%) and further impurities (further impurities=P—H compounds, oxide compounds, as yet incompletely converted chlorophosphite).

Procedure for the Catalysis Experiments

Experiment Description—General

In a 100 ml autoclave from Parr Instruments, various olefins were hydroformylated at various temperatures and synthesis gas pressure 20 or 50 bar (CO/H$_2$=1:1 (% by vol.)). As precursor, 0.005 g of Rh(acac)(CO)$_2$ was initially charged for a catalyst concentration of 40 ppm of Rh based on the overall reaction mixture, and correspondingly 0.0123 g of Rh(acac)(CO)$_2$ for a concentration of 100 ppm of Rh. The solvent used was 40 to 46 g of toluene in each case. Ligand 1 was used in different molar excesses relative to rhodium. In addition, as GC standard, about 0.5 g of tetraisopropylbenzene (TIPB) was added. About 6 g of reactant were metered in after the reaction temperature envisaged had been attained.

During the reaction, the pressure was kept constant via metered addition of synthesis gas with a mass flow meter and pressure regulator. The stirrer speed was 1200 min$^{-1}$. Samples were taken from the reaction mixture after 12 hours. The results of the experiments are summarized in Table 8 (yield=total yield of aldehyde and alcohol; S=selectivity for the linear product).

(acac=acetylacetonate)

TABLE 8

| Entry | Starting material | p in [bar] | cRh in ppm | P: Rh | Yield in % | S (n-aldehyde) in % |
|---|---|---|---|---|---|---|
| 1 | cis-2-butene | 20 | 40 | 4 | 58.0 | 45.3 |
| 2 | cis-2-butene | 50 | 40 | 4 | 96.5 | 40.7 |
| 3 | 1-butene | 20 | 40 | 4 | 49.2 | 51.9 |
| 4 | 1-butene | 50 | 40 | 2 | 97.4 | 46.8 |
| 5 | 1-butene | 50 | 92 | 8 | 99.5 | 50.3 |
| 6 | 1-octene | 50 | 40 | 9 | 97.1 | 43.2 |

Reaction conditions: ligand 1, reaction temperature 120° C.

Lines 1 and 2 list experiments on the rhodium-catalysed hydroformylation of the cis-2-butene reactant with ligand 1. At a synthesis gas pressure of 20 bar, in experiment 1, 58.0 mol % of pentanal is formed with a pentanal selectivity of 45.3%. The proportion of hydrogenation to the alkane is low at about 1.3% to 1.5%. The formation of pentanol is not observed. An increase in the synthesis gas pressure leads to a rise in the pentanal yield to 95.1 mol %, but the regioselectivity falls to about 40%.

Lines 3 to 5 list hydroformylations of 1-butene. At 20 bar (line 3), at a ligand excess of 4:1, a yield of about 49% and a selectivity for n-pentanal of about 52% are attained. At synthesis gas pressure 50 bar, a n-pentanal selectivity of 50% is obtained with virtually full conversion (lines 4 and 5). Alkane formation is low. In the experiment in line 4, the molar excess of ligand was reduced to about 2:1. The yield rises to 97.4%; the pentanal selectivity falls slightly to 46.8%. In line 5, the Rh concentration was increased to about 100 ppm and the ligand excess was increased to 8:1 relative to rhodium. The aldehyde yield rises to 99.5%; the regioselectivity likewise rises to 50.3%.

It is also possible to hydroformylate longer-chain olefins such as 1-octene with good n selectivity for the product (line 6).

Table 9 contains experiments on the hydroformylation of an n-octene mixture having about 2% 1-octene, 40%

2-octenes, 36% 3-octenes and 23% 4-octenes (yield=total yield of aldehyde and alcohol; S=selectivity for the linear n-pentanal product). In this case, the experiments were conducted both with the inventive ligand 1 and with the comparative TDTBPP ligand.

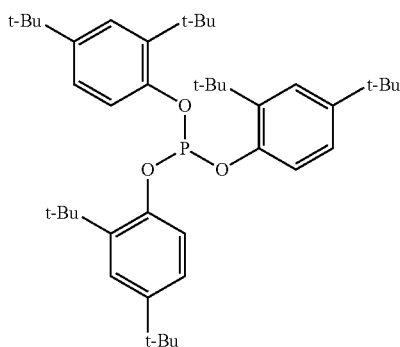 [SMILES: CC(C)(C)c1ccc(OP(Oc2ccc(C(C)(C)C)cc2C(C)(C)C)Oc2ccc(C(C)(C)C)cc2C(C)(C)C)c(C(C)(C)C)c1]

Tris(2,4-di-tert-butylphenyl)phosphite (TDTBPP)

TABLE 9

| Entry | T in [° C.] | cRh in ppm | P:Rh | Yield in % | S (linear product) in % |
|---|---|---|---|---|---|
| 1[a] | 80 | 90 | 20 | 99.0 | 7.2 |
| 2[a] | 80 | 90 | 5 | 99.0 | 11.1 |
| 3[a] | 90 | 90 | 20 | 99.2 | 10.6 |
| 4[b] | 90 | 280 | 20 | 97.9 | 4.7 |
| 5[a] | 100 | 50 | 20 | 99.0 | 15.4 |
| 6[b] | 100 | 90 | 20 | 96.4 | 6.9 |
| 7[a] | 110 | 90 | 20 | 99.2 | 16.5 |
| 8[b] | 110 | 90 | 20 | 99.0 | 9.7 |
| 9[a] | 120 | 90 | 20 | 95.2 | 22.9 |
| 10[b] | 120 | 90 | 20 | 99.0 | 14.4 |
| 11[a] | 130 | 90 | 20 | 98.0 | 30.5 |
| 12[b] | 130 | 76 | 20 | 98.8 | 23.9 |
| 13[a] | 140 | 90 | 20 | 97.4 | 31.6 |
| 14[b] | 140 | 56 | 20 | 98.0 | 23.9 |
| 15[a] | 120 | 90 | 4 | 98.9 | 28.8 |
| 16[a] | 120 | 40 | 9.5 | 98.6 | 29.1 |
| 17[a] | 120 | 40 | 20 | 99.1 | 28.2 |

Reaction conditions: 50 bar of synthesis gas (CO/H$_2$); substrate: n-octenes; a): ligand 1; b): ligand TDTBPP.

Entries 1 to 14 each show results of experiments at a constant temperature in the range from 80° C. to 140° C., in each case for the inventive ligand 1 and for the comparative ligand (TDTBPP). As is clearly apparent, the inventive ligand 1 in all cases shows a distinctly higher n selectivity for the desired product combined with very good overall yields. The formation of alkanes and alcohols is insignificant. If entries 13 and 14 are compared, ligand 1 has nearly an 8% increase in selectivity compared to the commercially available comparative ligand. Entries 15 to 17 show the use of ligand 1 with different molar excesses relative to rhodium. In all cases, it was possible to achieve very good n selectivities.

Table 10 gives the results for the hydroformylation of di-n-butene. Di-n-butene is a mixture of isomers of n-octenes (about 16%), 3-methylheptenes (about 65%) and 3,4-dimethylhexenes (about 19%) (yield=total yield of aldehyde and alcohol; S=selectivity for the linear product).

TABLE 10

| Entry | T in [° C.] | p in [bar] | cRh in ppm | P:Rh | Yield in % | S (nl)* in % |
|---|---|---|---|---|---|---|
| 1 | 120 | 50 | 40 | 10 | 85.1 | 30.8 |
| 2 | 120 | 50 | 90 | 7 | 89.8 | 28.3 |
| 3 | 120 | 50 | 90 | 7 | 91.5 | 30.9 |
| 4 | 120 | 50 | 100 | 5 | 93.0 | 36.5 |
| 5 | 120 | 50 | 75 | 20 | 94.6 | 29.8 |
| 6 | 130 | 50 | 75 | 20 | 95.3 | 32.7 |
| 7 | 110 | 50 | 75 | 20 | 91.9 | 24.0 |
| 8 | 120 | 40 | 75 | 20 | 94.8 | 29.0 |

Reaction conditions: ligand 1; substrate: di-n-butene
*Proportion of the aldehydes formed through terminal hydroformylation (essentially nonanal, 4-methyloctanal, 3-ethylheptanal, 6-methyloctanal, 4,5-dimethylheptanal and 3-ethyl-4-methylhexanal)

The above Table 10 contains experimental results for the rhodium-catalysed hydroformylation of di-n-butene with ligand 1. Entries 1 to 5 were conducted at 120° C. and 50 bar, and entry 8 at 40 bar. Entries 2 and 3 are a double determination with a ligand excess of 7 relative to rhodium and a rhodium concentration based on the overall reaction mixture of 80 ppm; entry 1 was performed at an excess of about 10:1 and an Rh concentration of 40 ppm. Entry 4 describes a reduction in the excess to 5:1 compared to entries 2 and 3. Entries 5 to 8 are experiments with a high ligand excess of about 20:1. Entries 5 to 7 were conducted at different temperatures. Entry 8 differs from entry 5 by the pressure. Analogously to the experiments with the n-octene mixture, high n selectivities between 28 and 36 mol % are found in all of experiments 1 to 6 and 8. At lower temperature (entry 7), the n selectivity is reduced to about 24%. n-Octenes are converted virtually quantitatively within the experimental duration of 12 hours; the conversion of the 3-methylheptenes is >96%. The 3,4-dimethylhexenes are converted to an extent of 73%-86%. It was thus possible to show with the aid of the above examples that the novel catalyst system is also suitable for hydroformylation of technical olefin mixtures containing mainly branched olefins containing internal double bonds, and a high proportion of desired terminally hydroformylated products can be obtained.

Table 11 gives the results for the hydroformylation of n-octenes with ligand 3 (yield=total yield of aldehyde and alcohol; S=selectivity for the linear product).

TABLE 11

| Entry | T in [° C.] | Yield in % | S (linear product) in % |
|---|---|---|---|
| 1 | 80 | 30.0 | 8.6 |
| 2 | 90 | 85.9 | 4.9 |
| 3 | 100 | 91.3 | 5.9 |
| 4 | 110 | 98.5 | 8.3 |
| 5 | 120 | 99.0 | 11.9 |

Reaction conditions: ligand 3; 50 bar of synthesis gas; substrate: n-octenes; cRh = 90 ppm; L/Rh = 20.

The above table contains a compilation of the experimental data for the hydroformylation of n-octenes with ligand 3 in the form of a temperature series from 80° C. to 120° C. at synthesis gas pressure 50 bar, an Rh concentration of about 100 ppm and a ligand excess of about 20:1. The n-nonanal selectivities in this series of experiments are low at 4.9 to 11.9 mol %, but the aldehyde yields at higher temperatures are virtually quantitative and very good. Alkane formation is low at <1%; hydrogenation to alcohols is not observed.

Table 12 gives the results for the hydroformylation of di-n-butene. Di-n-butene is a mixture of isomers of n-octenes (about 16%), 3-methylheptenes (about 65%) and 3,4-dimethylhexenes (about 19%) (yield=total yield of aldehyde and alcohol; S=selectivity for the linear product).

TABLE 12

| Entry | Ligand | T in [° C.] | p in [bar] | cRh in ppm | P:Rh | Yield in % |
|---|---|---|---|---|---|---|
| 1 | 4 | 140 | 50 | 100 | 20:1 | 38 |
| 2 | 3 | 140 | 50 | 100 | 10:1 | 74 |
| 3 | 5 | 120 | 50 | 100 | 20:1 | 85 |
| 4 | 5 | 130 | 50 | 100 | 20:1 | 86 |
| 5 | 5 | 140 | 50 | 100 | 20:1 | 96 |
| 6 | 5 | 140 | 50 | 100 | 15:1 | 97 |
| 7 | 5 | 140 | 50 | 100 | 5:1 | 97 |

Reaction conditions: ligand 1; substrate: di-n-butene
*Proportion of the aldehydes formed through terminal hydroformylation (essentially nonanal, 4-methyloctanal, 3-ethylheptanal, 6-methyloctanal, 4,5-dimethylheptanal and 3-ethyl-4-methylhexanal)

The above Table 12 contains experimental results for the rhodium-catalysed hydroformylation of di-n-butene with ligands 3, 4 and 5. While ligand 4 (entry 1) gives a moderate overall yield of aldehydes and alcohols, ligands 3 and 5 are notable for very good yields. Especially ligand 5 shows virtually quantitative yields at elevated temperature (140° C.) (entries 5 to 7).

It was thus possible to show with the aid of the above examples that the novel catalyst system is also suitable for hydroformylation of technical olefin mixtures containing mainly branched olefins containing internal double bonds, and a high proportion of desired hydroformylated products can be obtained.

The inventive monophosphite ligands have a very good n selectivity in relation to the hydroformylation. Selectivity for the desired linear aldehydes is much greater here than, for example, in the case of the commercially available TDTBPP ligand. The stated objects are therefore achieved by these novel inventive ligands.

German patent application 102014209532.8 filed May 20, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A ligand having structure I or II:

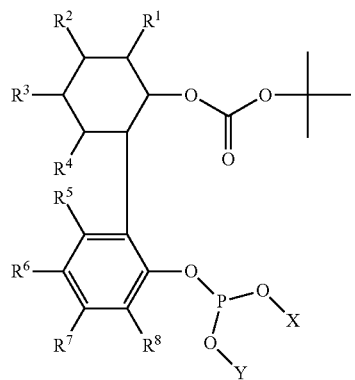

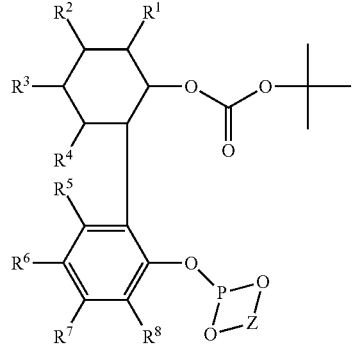

wherein
$R^1$, $R^2$, $R^3$, $R^4$, $R^5$, $R^6$, $R^7$, $R^8$ are each independently selected from the group consisting of: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, and —N[($C_1$-$C_{12}$)-alkyl]$_2$;

X and Y are each independently selected from the group consisting of
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, and —($C_5$-$C_8$)-cycloalkyl-($C_4$-$C_{20}$)-aryl-CO—($C_6$-$C_{20}$)-aryl, Z is selected from the group consisting of
—($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_{20}$)-aryl-, —($C_4$-$C_{20}$)-heteroaryl-, —($C_6$-$C_{20}$)-aryl-CO—($C_6$-$C_{20}$)-aryl-, and —($C_6$-$C_{20}$)-aryl-($C_6$-$C_{20}$)-aryl-;

wherein the alkyl, heteroalkyl, cycloalkyl, heterocycloalkyl, aryl and heteroaryl groups mentioned are optionally substituted.

2. The ligand according to claim 1, wherein X and Y are each independently selected from the group consisting of
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, and —($C_4$-$C_{20}$)-heteroaryl-($C_1$-$C_{12}$)-alkyl.

3. The ligand according to claim 1, wherein X and Y are each independently selected from the group consisting of
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, and —($C_6$-$C_{20}$)-aryl-COO—($C_1$-$C_{12}$)-alkyl.

4. The ligand according to claim 1, wherein Z is selected from the group consisting of
—($C_1$-$C_{12}$)-alkyl-, —($C_6$-$C_{20}$)-aryl-, —($C_6$-$C_{20}$)-aryl-($C_1$-$C_{12}$)-alkyl-, —($C_6$-$C_{20}$)-aryl-CO—($C_6$-$C_{20}$)-aryl-, —($C_1$-$C_{12}$)-alkyl-($C_6$-$C_{20}$)-aryl-, and —($C_6$-$C_{20}$)-aryl-($C_6$-$C_{20}$)-aryl-.

5. The ligand according to claim 1, wherein $R^1$, $R^2$, $R^3$, $R^4$, $R^5$, $R^6$, $R^7$, $R^8$ are each independently selected from the group consisting of —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$NH_2$, and —N[($C_1$-$C_{12}$)-alkyl]$_2$.

6. The ligand according to claim 1, wherein X and Y are the same radicals.

7. The ligand according to claim 1, wherein $R^3$ and $R^6$ are each —O—$(C_1$-$C_{12})$-alkyl.

8. The ligand according to claim 1, wherein $R^3$ and $R^6$ are each —OMe.

9. The ligand according to claim 1, wherein $R^1$ and $R^8$ are each —$(C_1$-$C_{12})$-alkyl.

10. The ligand according to claim 1, wherein R and $R^8$ are each tert-butyl.

11. The ligand according to claim 1, having the general structure III:

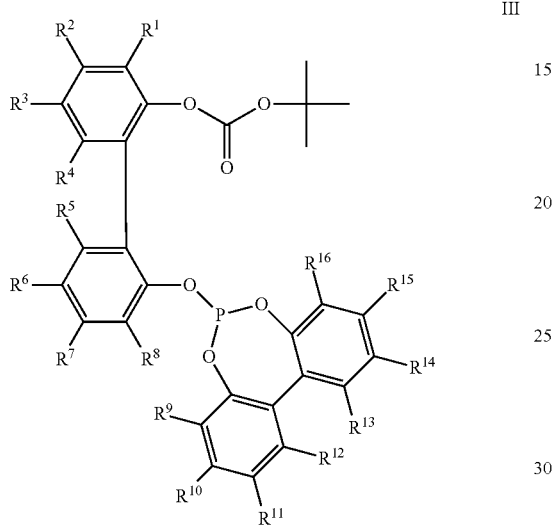

III wherein $R^9$, $R^{10}$, $R^{11}$, $R^{12}$, $R^{13}$, $R^{14}$, $R^{15}$, $R^{16}$ are each independently selected from the group consisting of —H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$SO_3H$, —$SO_3Na$, —$NO_2$, —CN, —$NH_2$, and —N[$(C_1$-$C_{12})$-alkyl]$_2$.

12. The ligand according to claim 1, having the general structure IV:

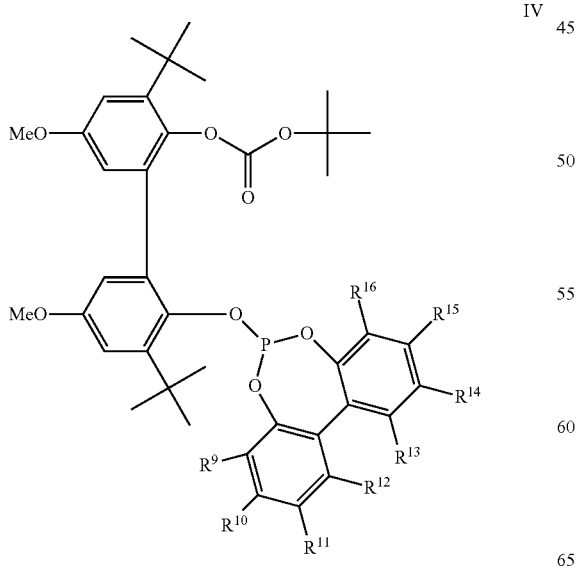

IV wherein $R^9$, $R^{10}$, $R^1$, $R^{12}$, $R^{13}$, $R^{14}$, $R^{15}$, $R^{16}$ are each independently selected from the group consisting of —H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$SO_3H$, —$SO_3Na$, —$NO_2$, —CN, —$NH_2$, and —N[$(C_1$-$C_{12})$-alkyl]$_2$.

13. The ligand according to claim 1, which has the structure I.

14. The ligand according to claim 1, which has the structure II.

15. The ligand according to claim 1, which has a structure selected from the group consisting of the following structures 1 to 70:

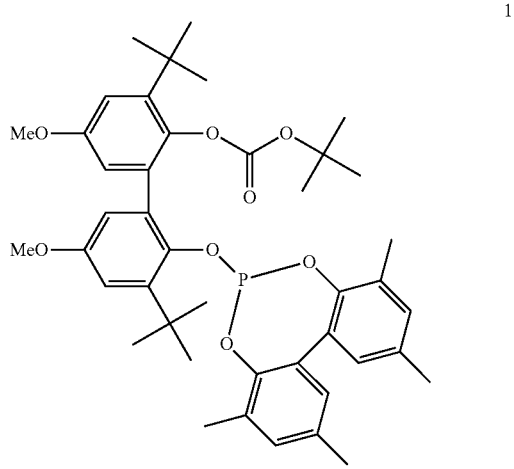

1

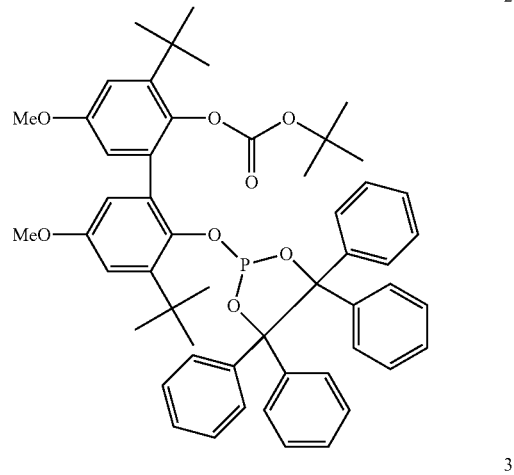

2

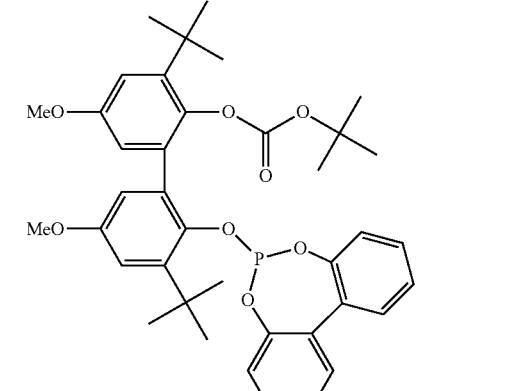

3

4
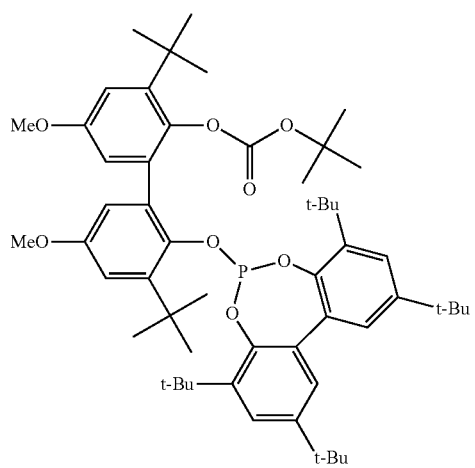
5
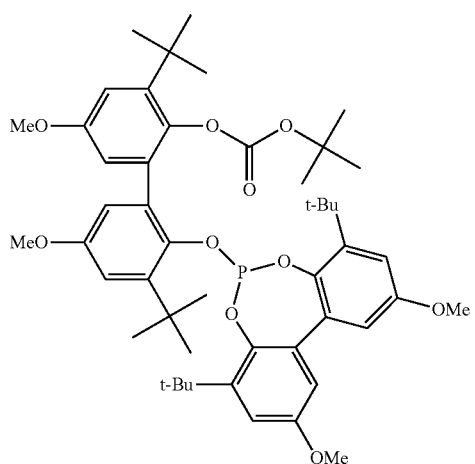
6
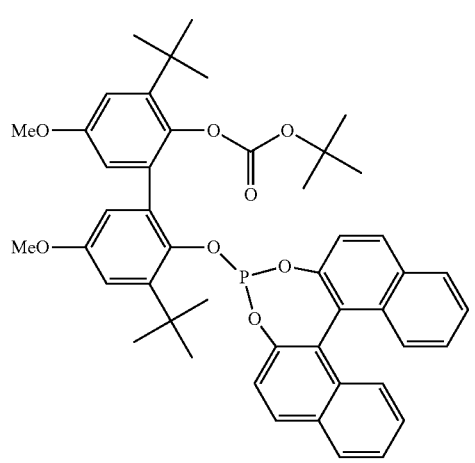
7
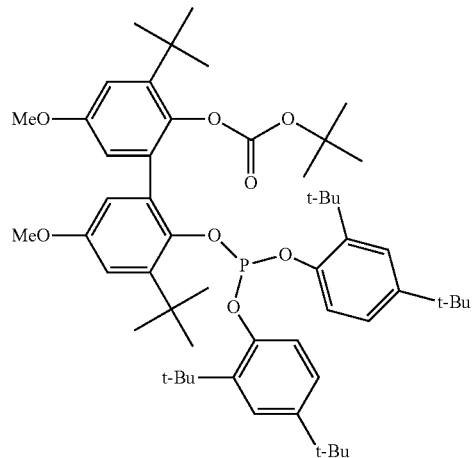
8
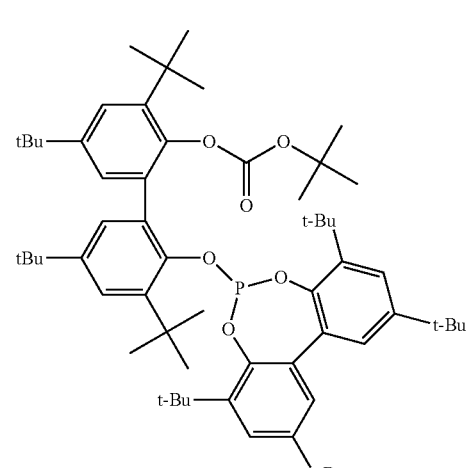
9
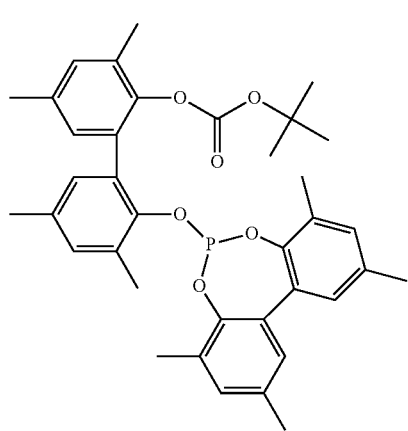

57
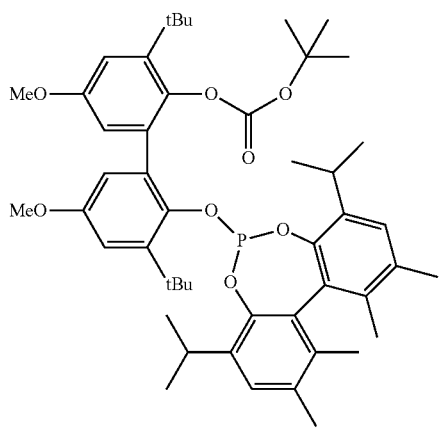
10
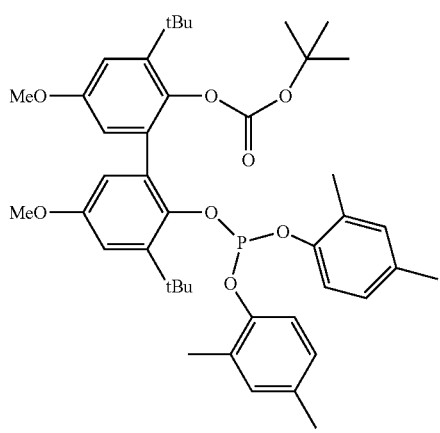
11
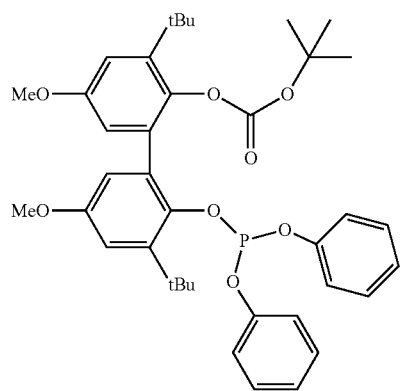
12
58
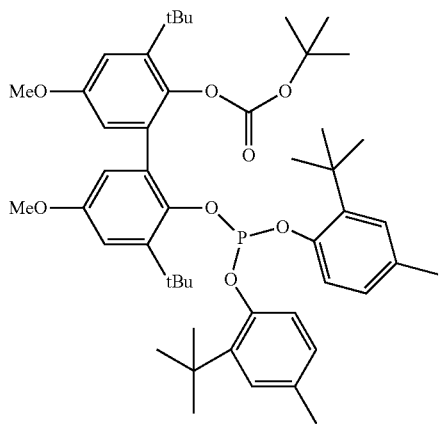
13
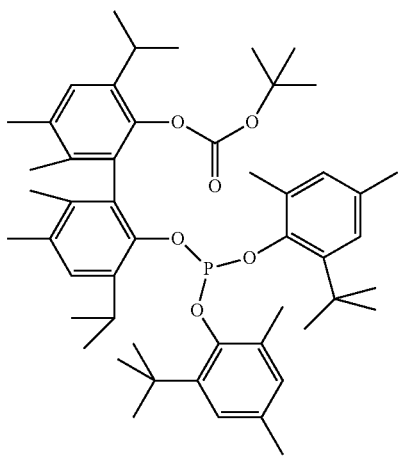
14
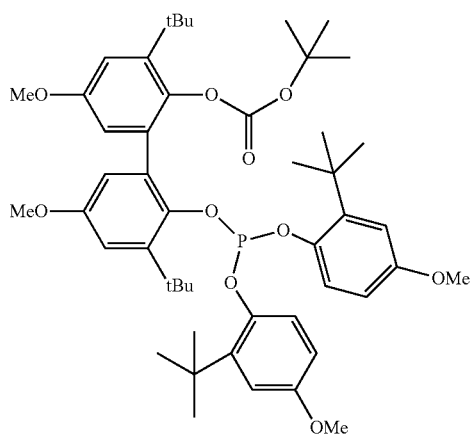
15

16
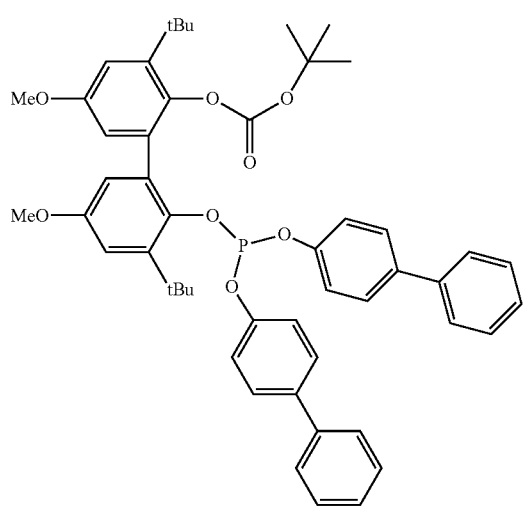
17
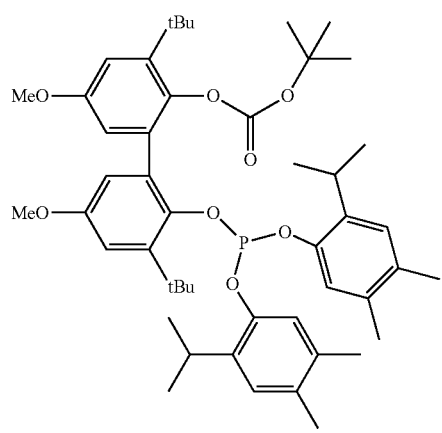
18
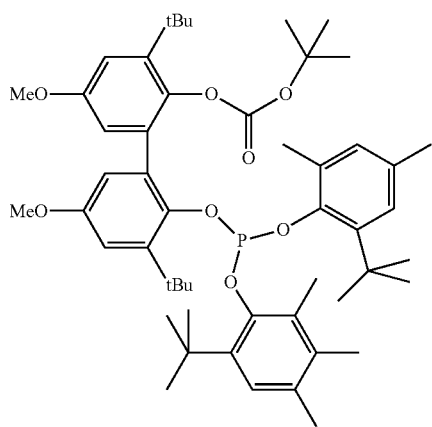
19
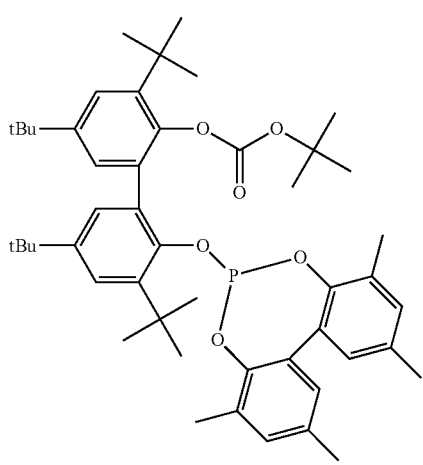
20
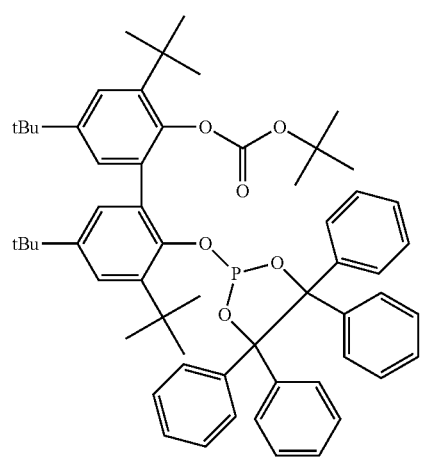
21
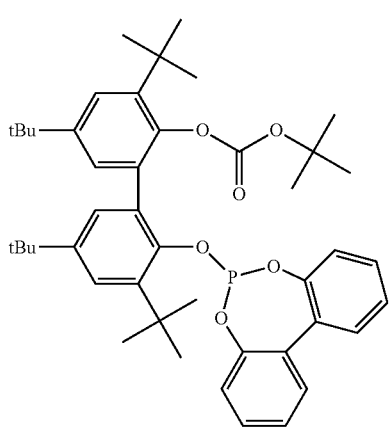

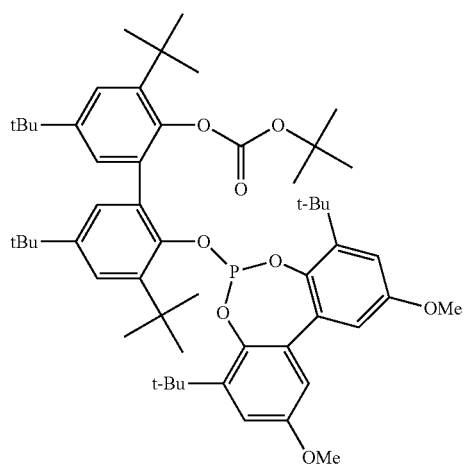
22
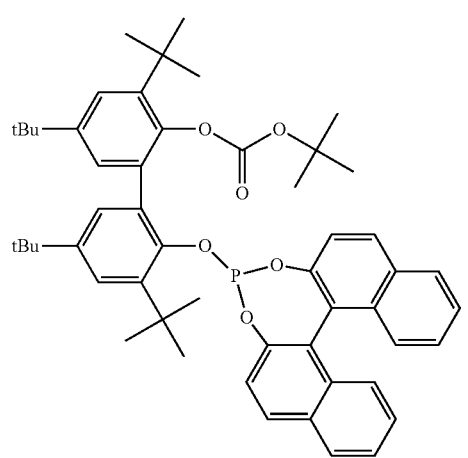
23
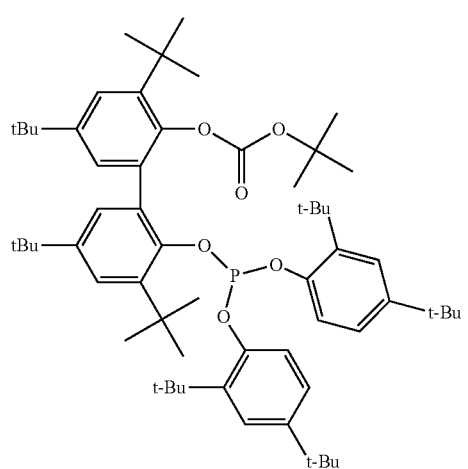
24
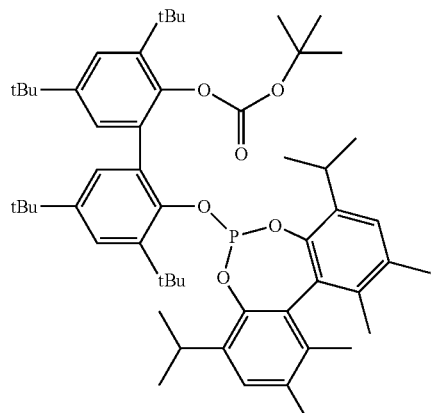
25
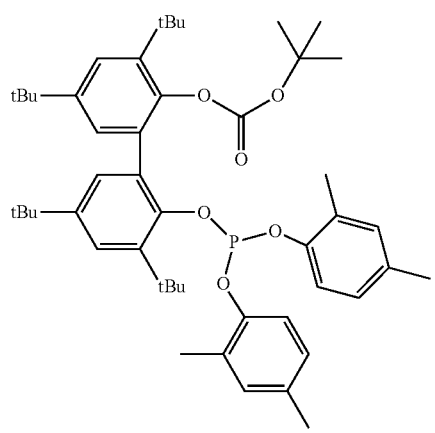
26
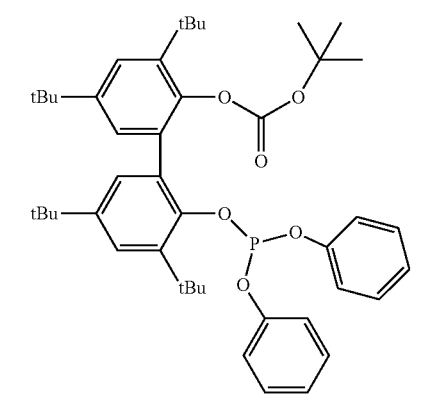
27
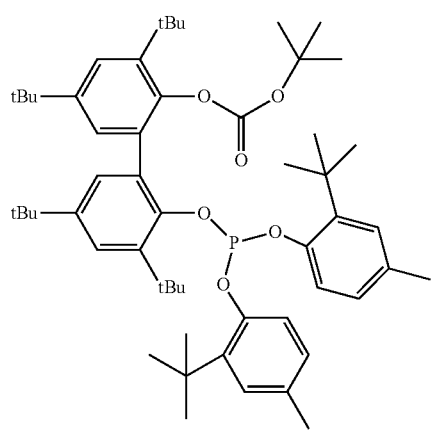
28

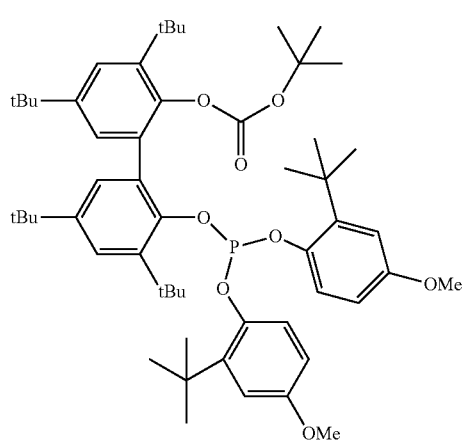
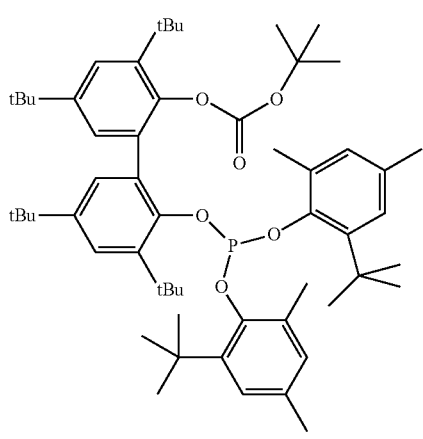

36
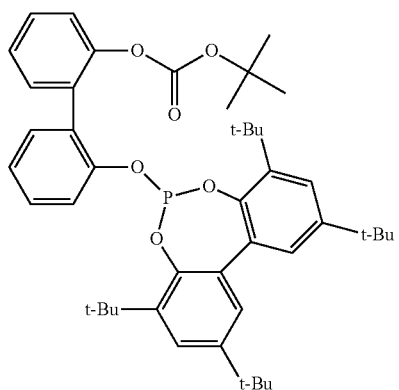
37
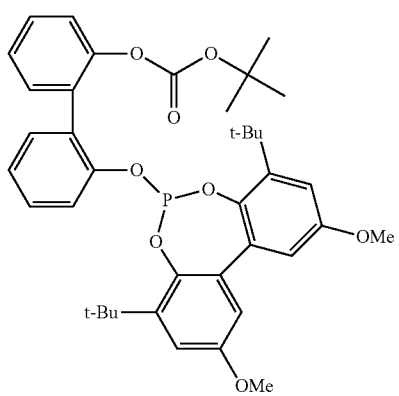
38
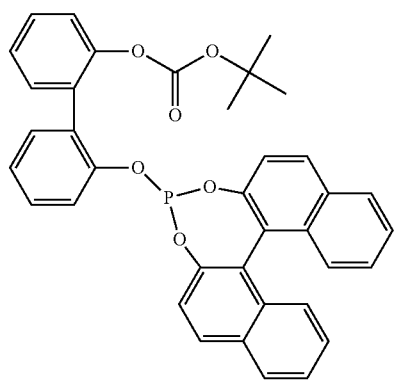
39
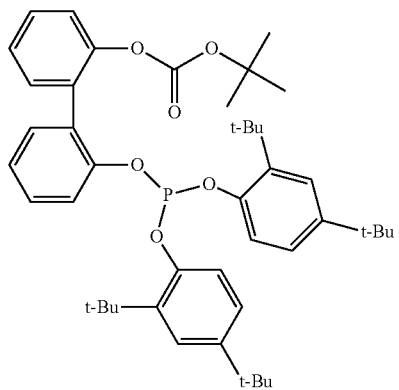
40
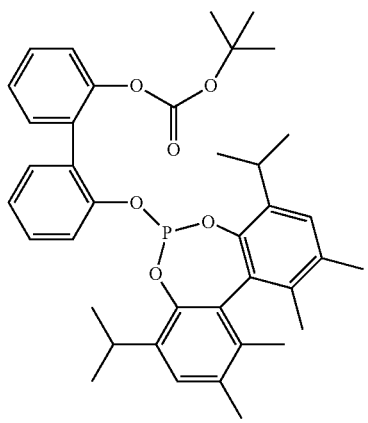
41
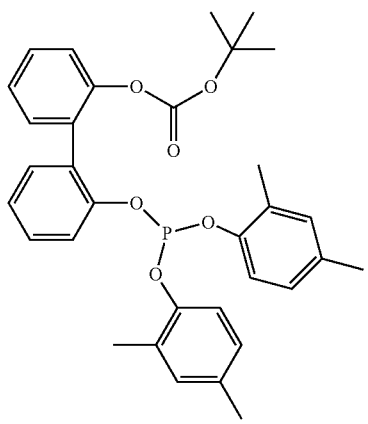
42
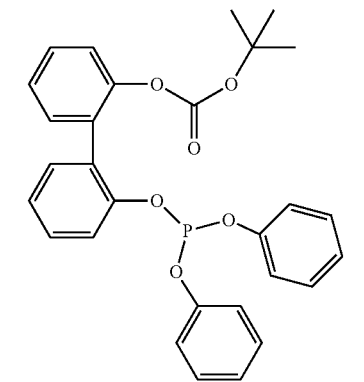
43
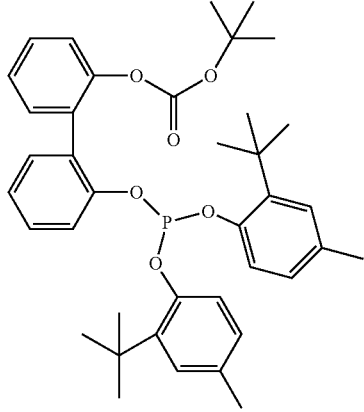

44
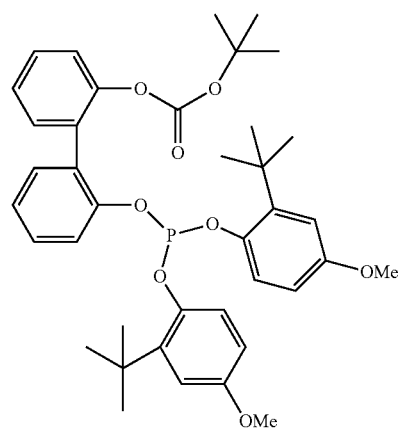
45
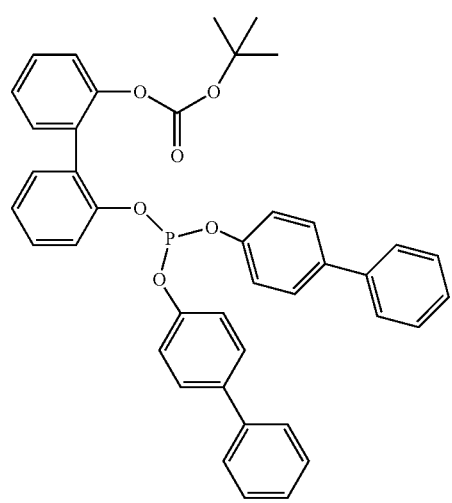
46
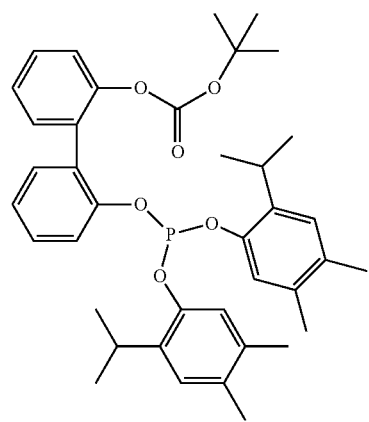
47
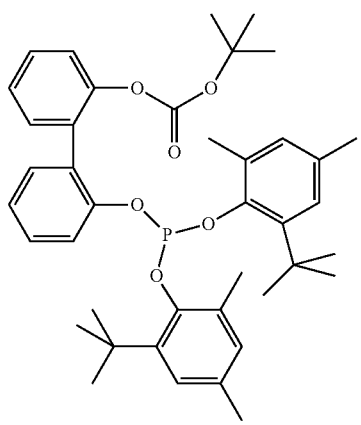
48
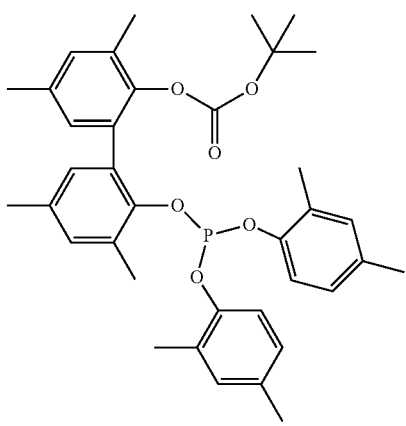
49
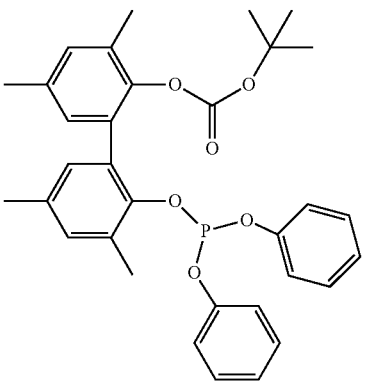
50
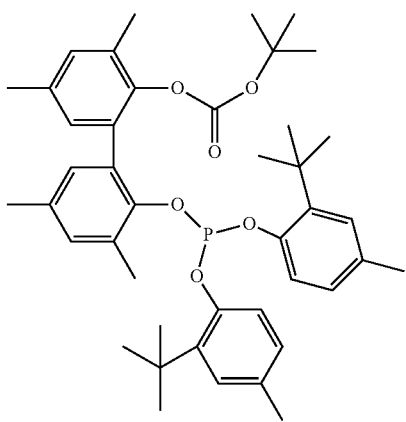

51
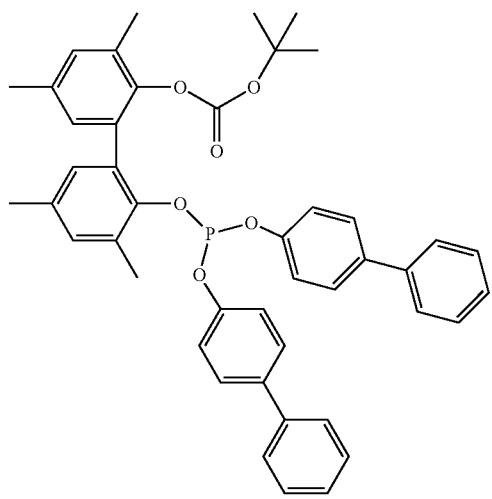
52
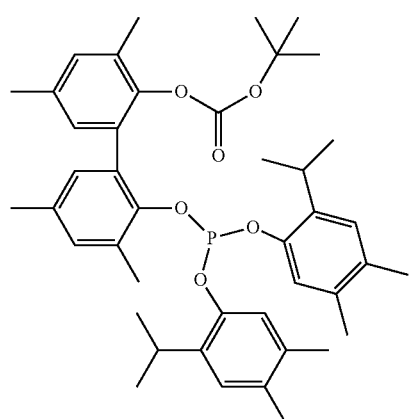
53
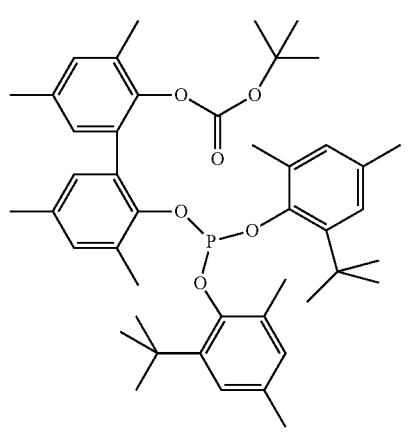
54
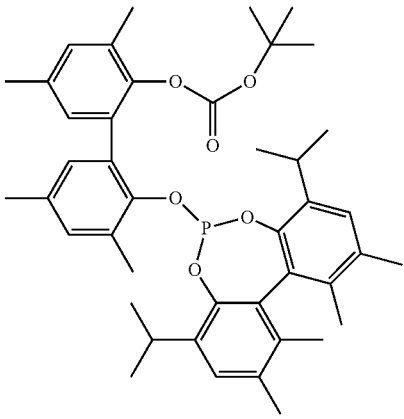
55
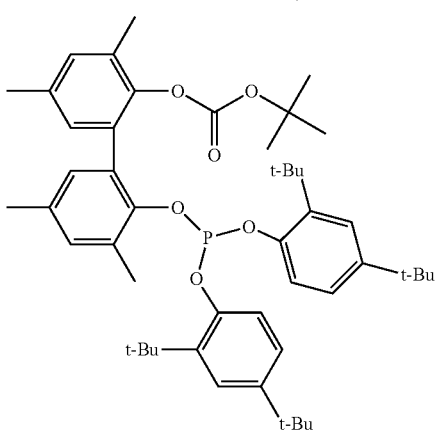
56
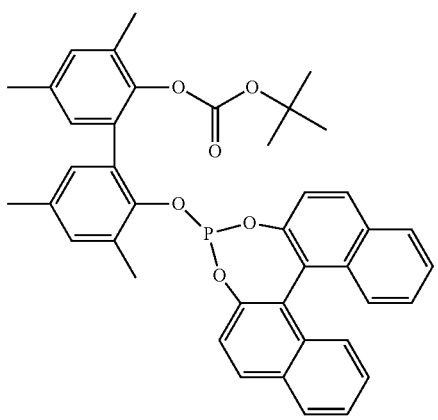
57
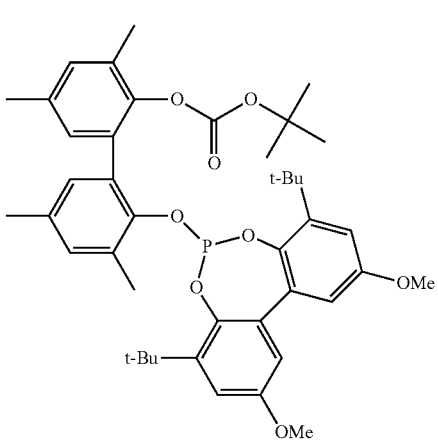

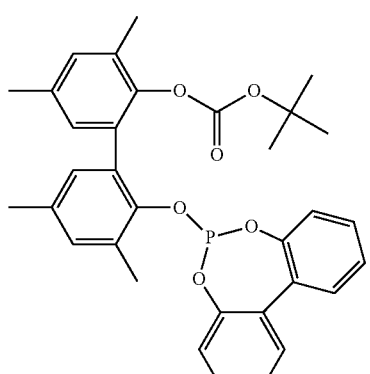
58
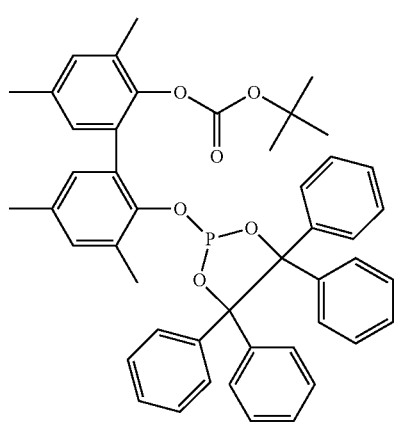
59
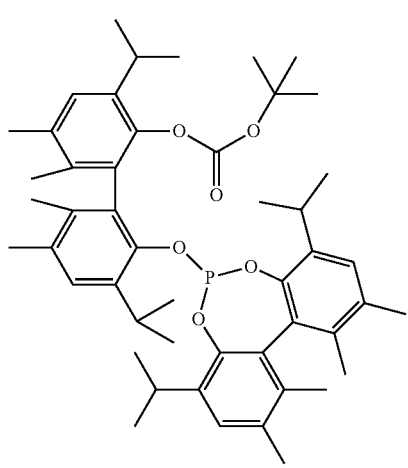
60
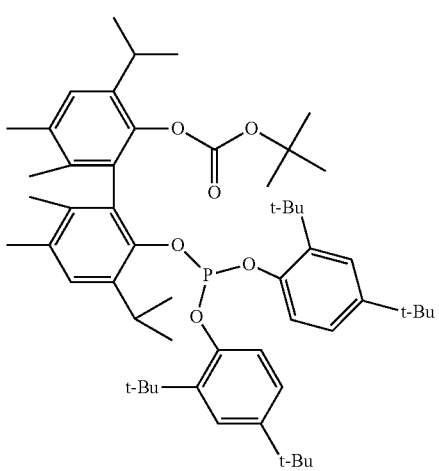
61
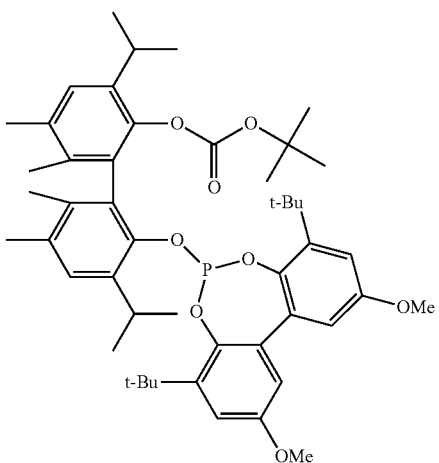
62

64
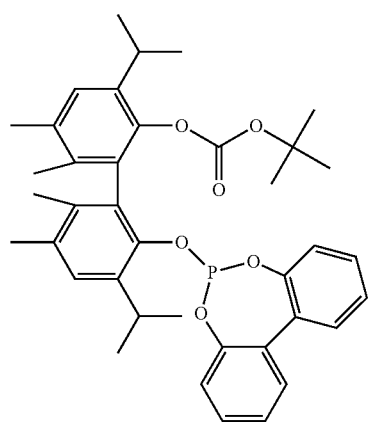
65
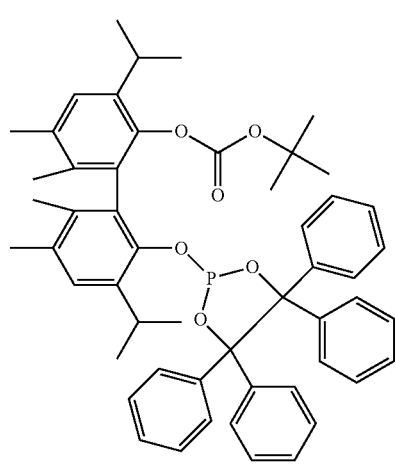
66
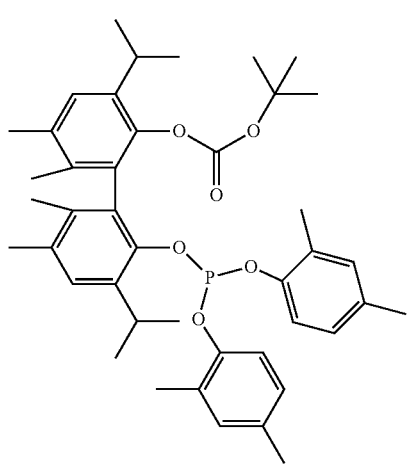
67
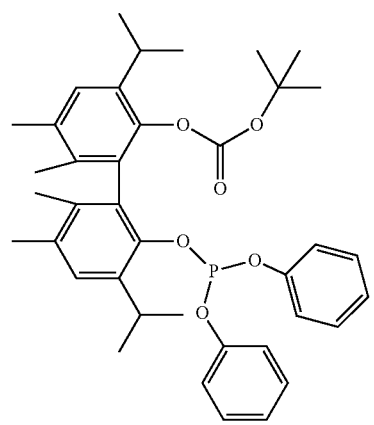
68
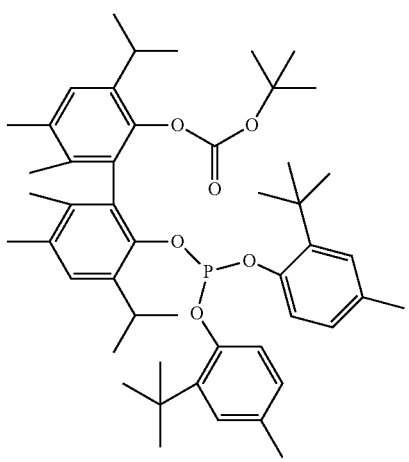
69
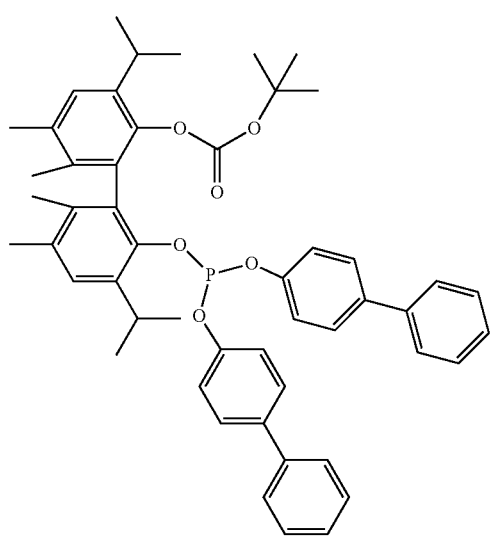

-continued

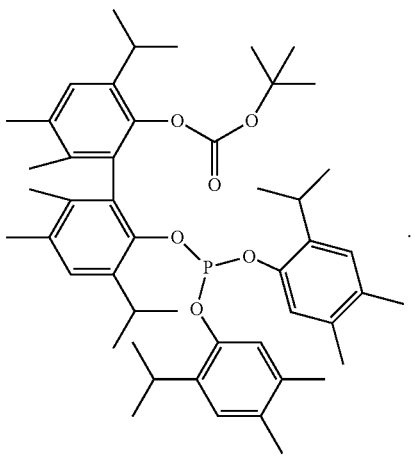

16. A complex, comprising:
the ligand according to claim 1, and
a metal atom selected from the group consisting of Rh, Ru, Co, and Ir.

17. A process for the hydroformylation of an olefin, comprising:
  a) initially charging an olefin,
  b) adding
    the complex according to claim 13, to obtain a reaction mixture,
  c) feeding $H_2$ and CO into the reaction mixture,
  d) heating the reaction mixture, to obtain conversion of the olefin to an aldehyde.

18. A process for the hydroformylation of an olefin, comprising:
  a) initially charging an olefin,
  b) adding a ligand according to claim 1 and a compound including a metal atom selected from the group consisting of Rh, Ru, Co, and Ir, to obtain a reaction mixture,
  c) feeding $H_2$ and CO into the reaction mixture,
  d) heating the reaction mixture, to obtain conversion of the olefin to an aldehyde.

* * * * *